United States Patent [19]
Brown et al.

[11] Patent Number: 5,843,641
[45] Date of Patent: Dec. 1, 1998

[54] METHODS FOR THE DAIGNOSIS, OF FAMILIAL AMYOTROPHIC LATERAL SCLEROSIS

[75] Inventors: Robert Brown, Needham; H. Robert Horvitz, Cambridge; Daniel R. Rosen, Dedham, all of Mass.

[73] Assignees: Massachusetts Institute of Technology, Cambridge; General Hospital Corporation, The, Boston, both of Mass.

[21] Appl. No.: 23,980

[22] Filed: Feb. 26, 1993

[51] Int. Cl.$^6$ .............................. C12Q 1/68; C12P 19/34; C07H 21/04
[52] U.S. Cl. ............................ 435/6; 435/91.2; 435/91.5; 435/91.51; 436/63; 436/811; 536/24.31; 536/24.33; 935/8; 935/77; 935/78
[58] Field of Search .............................. 435/6, 91.2, 91.5, 435/91.51; 436/63, 811; 536/24.31, 24.33; 935/77, 78, 8

[56] References Cited

U.S. PATENT DOCUMENTS

| | | | |
|---|---|---|---|
| 5,066,591 | 11/1991 | Hallewell et al. | 435/189 |
| 5,084,390 | 1/1992 | Hallewell et al. | 435/188 |
| 5,196,335 | 3/1993 | Groner | 435/240.2 |
| 5,240,847 | 8/1993 | Heckl | 435/189 |

FOREIGN PATENT DOCUMENTS

WO 92/05178   4/1992   WIPO .

OTHER PUBLICATIONS

Parbossingh et al, Archives Neurology (1995) 52: 1160–1163.
Morita et al, Neuroscience Letters (1996) 205: 79–82.
Gallagher et al., Genomico (1992, Feb. 25) 12: 610–612.
David et al, (Cr Acad Sci Panss (1988) 306: 1–4.
Nakano et al, Biochem Biophys Res Commun (1994) 200:695–703.
Beauchamp, C., et al., "Superioxide Dismutase: Improve Assays and an Assay Applicable to Acrylamide Gel," *Analytical Biochemistry*, 44: 276 (1971).
Beckman, J.S., et al., "Superoxide Dismutase and Catalase Conjugated to Polyethylene Glycol Increases Endothelial Enzyme Activity and Oxidant Resistance," *J. of Biological Chemistry*,263:6884 (1988).
Bracco, F., et al., "Determination of Superoxide Dismutase Activity by the Polargraphic Method of Catalytic Currents in The Cerebrospinal Fluid of Aging Brain and Neurologic Degenreative Diseases", *Superoxide Dismutase in CSF*,196:36 (1990).

Carlioz, A., et al.,"Isolation of superoxide dismutase mutants in *Escherichia coli*:is superoxide dismutase necessary for aerobic life?" *EMBO Journal*, 5:623 (1986).
Hallewell, R.A., et al., "Structure of the Human Cu/Zn SOD Gene,"*Superoxide and Superoxide Dismutase* in Chemistry, Biology and Medicine, p. 249 (1986).
Hallewell, B., "Oxidants and human disease: some new concepts", *FASEB Journal* , 1:358 (1987).
Hartmann, H.A., et al., "Deficiency of Copper Can Cause Neuronal Degeneration," *Medical Hypotheses*38:75 (1992).
Hjalmarsson, K., et al., "Isolation and sequence of complemtary DNA encoding human extracellular superoxide dismutase," *Proc. Natl. Acad. Sci. USA*,84:6340 (1987).
Huang, T.T., et al., "Relationship of resistance to oxygen free radicals to CuZn–superoxide dismutase activity in transgeneic, transfected, and trisomic cells," *FASEB Journal*,6:903 (1992).
Hudson, A.J. "Amyotrophic Laternal Sclerosis and its Association with Desmentia, Parkinsonism and other Neurological Disorders: A Review," *Brain,*104:217 (1981).
Imlay, J.A., et al. "Toxic DNA Damage by Hydrogen Peroxide Through the Fenton Reaction in Vivo and in Vitro," *Science,* 240:640 (1988).
Levanon, D., et al. "Architecture and anatomy of the chromosomal Locus in human chromosome 21 encoding the Cu/Zn superoxide dismutase," *EMBO Journal,*4:77 (1985).
Liu, T.H., et al., Polyethylene glycol–conjugated superoxide dismutase and catalase reduce ischemic brain injury,*American Journal of Physiology,*256:589 (1989).
McCord, J.M, et al., "Superoxide Dismutase, an Enzymic Function for Erythrocuprein (Hemocuprein)," *Journal of Biological Chemistry,*244:6049 (1969).
Olanow, C.W., "An Introduction to the Free Radical Hypothesis in Parkinson's Disease," *Annals of Neurology,*32:S2 (1992).
Oury, T.D., et al., "Extracellular superoxide dismutase, nitric oxide, and central nervous system $O_2$ $_{toxicity,"}$ *Proc. Natl. Acad. Sci. USA,*89:9715 (1992).
Siddique, T., et al., "Linkage of a Gene Causing Familial Amyotrophic Lateral Sclerosis to Chromosome 21 and Evidence of Genetic–Locus Heterogeneity," *New England Journal of Medicine,*324:1381 (1991).
Wispé, J.R., et al., "Synthesis and processing of the precursor for human mangano–superoxide dismutase," *Biochimica et Biophysica Acta.*994:30 (1989).

*Primary Examiner*—Carla J. Myers
*Attorney, Agent, or Firm*—Kristina Bieker-Brady, Ph.D; Clark & Elbing LLP

[57] ABSTRACT

Disclosed is the family of genes responsible for the neurodegenerative diseases, particularly Amyotrophic Lateral Sclerosis. Methods and compounds for the diagnosis, prevention, and therapy of the disease are also disclosed.

23 Claims, 12 Drawing Sheets

Fig. 1C

Exon 2

| | | | | | | | | | | | | | | | | | | | | |
|---|---|---|---|---|---|---|---|---|---|---|---|---|---|---|---|---|---|---|---|---|
| FALS | | | | | | | | | S | D | R | | | | | | | | | |
| human | E | S | N | G | P | V | K | V | W | G | S | I | H | G | L | T | E | G | R | V | L | H | V | H | E | F | G | D | N | T | A | SEQ ID NO:15 |
| cow | A | S | G | D | T | V | V | L | T | G | T | I | K | G | L | T | E | G | L | H | G | F | H | V | H | Q | F | G | D | N | T | Q | SEQ ID NO:16 |
| pig | G | E | K | E | P | V | V | V | L | S | G | I | I | H | G | L | T | E | G | D | H | G | F | H | V | H | Q | F | G | D | N | T | Q | SEQ ID NO:17 |
| mouse | A | S | G | N | T | P | V | K | V | S | G | E | I | H | G | L | T | K | G | P | H | G | F | H | V | H | E | F | G | D | N | T | N | SEQ ID NO:18 |
| swordfish | G | N | A | V | G | K | V | T | F | T | Q | E | V | L | G | L | T | P | G | T | H | G | F | H | V | H | Q | Y | G | D | N | T | N | SEQ ID NO:19 |
| Drosophila | S | T | P | L | P | T | T | V | V | G | I | H | E | V | L | G | L | A | K | G | L | H | G | F | H | V | H | E | F | G | D | T | T | N | SEQ ID NO:20 |
| Onchocerca | K | E | G | L | P | T | T | V | K | G | N | L | V | L | G | L | T | K | P | G | L | H | G | F | H | V | H | Q | F | G | D | T | T | N | SEQ ID NO:21 |
| tomato | G | V | A | P | T | T | V | T | G | T | I | E | V | S | G | L | L | P | G | L | H | G | F | H | V | H | A | L | G | D | T | T | N | SEQ ID NO:22 |
| spinach | D | D | G | V | A | T | V | Y | I | V | Q | I | R | G | L | A | P | G | L | H | G | F | H | L | H | E | F | G | D | T | T | N | SEQ ID NO:23 |
| S. cerevisiae | S | E | S | E | P | T | T | V | S | Y | E | I | A | G | N | S | P | N | A | E | R | G | F | H | I | H | E | F | G | D | A | T | N | SEQ ID NO:24 |

Exon 4

| | | | | | | | | | | | | | | | | | | | | |
|---|---|---|---|---|---|---|---|---|---|---|---|---|---|---|---|---|---|---|---|---|
| FALS | | | | | | | | | | | | | | | | | | | | | |
| human | H | V | G | D | L | G | N | V | T | A | D | K | D | G | V | A | D | V | S | I | E | D | S | V | I | S | L | S | G | D | H | C | I | I | G | R | T | L | V | V | SEQ ID NO:25 |
| cow | H | V | G | D | L | G | N | V | T | A | G | K | D | G | V | A | N | V | S | I | E | D | R | V | I | S | L | S | G | E | Y | S | I | H | G | R | T | M | V | V | SEQ ID NO:26 |
| pig | H | V | G | D | L | G | N | V | T | A | D | K | D | G | V | A | D | V | S | I | E | D | S | V | I | S | L | S | G | D | H | S | I | I | G | R | T | M | V | V | SEQ ID NO:27 |
| mouse | H | V | G | D | L | G | N | V | T | A | G | K | D | G | V | A | T | V | Y | I | E | D | S | I | I | S | L | T | G | P | H | S | I | I | G | R | T | M | V | V | SEQ ID NO:28 |
| swordfish | H | L | G | D | L | G | N | I | E | A | T | G | D | C | P | T | A | A | K | H | T | T | H | V | T | D | S | F | L | G | P | N | S | I | V | G | R | T | V | V | SEQ ID NO:29 |
| Drosophila | E | A | G | D | L | G | N | I | E | A | G | A | D | G | V | A | K | I | D | I | E | D | R | L | I | S | L | T | G | Q | H | S | I | I | G | R | A | L | V | V | SEQ ID NO:30 |
| Onchocerca | H | A | G | D | L | G | N | I | V | A | N | T | D | D | G | V | A | E | T | H | V | T | D | K | H | Q | P | L | I | K | H | I | P | T | S | I | I | G | R | A | L | V | V | SEQ ID NO:31 |
| tomato | H | V | G | D | M | G | N | V | K | T | D | E | N | G | V | A | K | G | S | F | K | D | S | L | I | K | L | I | G | P | T | S | V | V | G | R | S | V | V | V | SEQ ID NO:32 |
| spinach | | | | | | | | | | | | | | | | | | | | | | | | | | | | | | | | | | | | | | | | | SEQ ID NO:33 |
| S. cerevisiae | | | | | | | | | | | | | | | | | | | | | | | | | | | | | | | | | | | | | | | | | SEQ ID NO:34 |

```
-552 GAATTCTGCC AACCAAATAA GAAACTCTAT ACTAAGGACT AAGAAAATTG
-502 CAGGGGAAGA AAAGGTAAGT CCCGGGATTG AGGTGTAGCG ACTTTCTATA
-452 CCCTCAGAAA ACTAAAAAAC AAGACAAAAA AATGAAAACT ACAAAAGCAT
-402 CCATCTTGGG GCGTCCCAAT TGCTGAGTAA CAAATGAGAC GCTGTGGCCA
-352 AACTCACGTC ATAACTAATG ACATTTCTAG ACAAAGTGAC TTCAGATTTT
-302 CAAAGCGTAC CCTGTTTACA TCATTTTGCC AATTTCGCGT ACTGCAACCG
-252 GCGGGCCACG CCCCCGTGAA AAGAAGGTTG TTTTCTCCAC ATTTCGGGGT
-202 TCTGGACGTT TCCCGGCTGC GGGGCGGGGG GAGTCTCCGG CGCACGCGGC
-152 CCCTTGGCCC CGCCCCCAGT CATTCCCGGC CACTCGCGAC CCGAGGCTGC
-102 CGCAGGGGGC GGGCTGAGCG CGTGCGAGGC GATTGGTTTG GGGCCAGAGT
 -52 GGGCGAGGCG CGGAGGTCTG GCCTATAAAG TAGTCGCGGA GACGGGGTGC
  -2 TG
   1 GTTTGCGTCG TAGTCTCCTG CAGCGTCTGG GGTTTCCGTT GCAGTCCTCG

51 GAACCAGGAC CTCGGCGTGG CCTAGCGAGT T ATG GCG ACG AAG GCC
                                       met ala thr lys ala
  97 GTG TGC GTG CTG AAG GGC GAC GGC CCA GTG CAG GGC ATC ATC
   6 val cys val leu lys gly asp gly pro val gln gly ile ile 139 AAT TTC GAG CAG AAG      GCAAGGG CTGGGACGGG AGGCTTGTGG
  20 asn phe glu gln lys     intron 1

TTGCGAGGCC GCTCCCGACC CGCTCGTCCC CCGCGACCC TTTGCATGGA
     CGGGTCGCCC GCCAGGG.........................
     CCTAGAGCAG GTTAAGCAGC TTGCTGGAGG TTCACTGGCT AGAAAGTGGT
     CAGCCTGGGA TTTGGACACA GATTTTTCCA CTCCCAAGTC TGGCTGCTTT
     TTACTTCACT GTGAGGGGTA AAGGTAAATC AGCTGTTTTC TTTGTTCAGA
     AACTCTCTCC AACTTTGCAC TTTTCTTAAA G
```

Fig. 2-1

```
154 GAA AGT AAT GGA CCA GTG AAG GTG TGG GGA AGC ATT AAA GGA
 26 glu ser asn gly pro val lys val trp gly ser ile lys gly 196 CTG ACT GAA GGC CTG CAT GGA TTC CAT GTT CAT GAG TTT GGA
 40 leu thr glu gly leu his gly phe his val his glu phe gly 238 GAT AAT ACA GCA G      GTCGGGTGTT.....................
 54 asp asn thr ala        intron 2

GTGTTTCTTT TTAGAATGTA TTTGGGAACT TTAATTCATA ATTTAGCTTT

TTTTTCTTCT TCTTATAAAT AG

251  GC TGT ACC AGT GCA GGT CCT CAC TTT AAT CCT CTA TCC AGA
 58 gly cys thr ser ala gly pro his phe asn pro leu ser arg 292 AAA CAC GGT GGG CCA AAG GAT GAA GAG AG      GTAACAAGAT
 72 lys his gly gly pro lys asp glu glu arg      intron 3

GCTTAACTCT TGTAATAATg gccGATCATG gTTCTGGAGT TCATATGGTA

TACTACTTGT AAATATGTGC TAAGATAATT CCGTGTTTCC CCCACCTTTG

CTTTTGAACT TGCTGACTCA TCTAAACCCT GCTCCCAAAT GCTGGAATGC

TTTTACTTCC TGGGCTTAAA GGAATTGACA AATGGGCACT TAAAACGATT

TGGTTTTGTA GCATTTGATT GAATATAGAA CTAATACAAG TGCCAAAGGG

GAACTAATAC AGGAAATGTT CATGAACAGT ACTGTCAACC ACTAGCAAAA

TCAATCATCA TT..............................

GTACTTCTGA AATCAGGTGC AGCCCCATCT TTCTTCCCAG AGCATTAGTG

TGTAGACGTG AAGCCTTGTT TGAAGAGCTG TATTTAGAAT GCCTAGCTAC

TTGTTTGCAA ATTTGTGTCC TACTCAGTCA AGTTTTAATT TAGCTCATGA

ACTACCTTGA TGTTTAGTGg CATCAGCCCT AATCCATCTG ATGCTTTTTC

ATTATTAG

321   G CAT GTT GGA GAC TTG GGC AAT GTG ACT GCT GAC AAA GAT
 82     his val gly asp leu gly asn val thr ala asp lys asp 361 GGT GTG GCC GAT GTG TCT ATT GAA GAT TCT GTG ATC TCA CTC
 95 gly val ala asp val ser ile glu asp ser val ile ser leu 403 TCA GGA GAC CAT TGC ATC ATT GGC CGC ACA CTG GTG
109 ser gly asp his cys ile ile gly arg thr leu val
```

Fig. 2-2

```
              GTAAG TTTTCATAAA AGGATATGCA TAAAACTTCT TCTAACATAC
              intron 4

AGTCATGTAT CTTTTCACTT TGATTGTTAG TCGCGGTTTC TAAGATCCAG

ATAAACTGT................................................

GAAAAAGCTT TGAGTAGTAG TTTCTACTTT TAAACTACTA AATATTAGTA

TATCTCTCTA CTAGGATTAA TGTTATTTTT CTAATATTAT GAGGTTCTTA

AACATCTTTT GGGTATTGTT GGGAGGAGGT AGTGATTACT TGACAGCCCA

AAGTTATCTT CTTAAAATTT TTTACAG

444     GTC CAT GAA AAA GCA GAT GAC TTG GGC AAA GGT GGA AAT GAA
121     val his glu lys ala asp asp leu gly lys gly gly asn glu 486     GAA AGT ACA AAG ACA GGA AAC GCT GGA AGT CGT TTG GCT TGT
135     glu ser thr lys thr gly asn ala gly ser arg leu ala cys 528     GGT GTA ATT GGG ATC GCC CAA TAA   ACATTCCCT TGGATGTAGT
149     gly val ile gly ile ala gln

CTGAGGCCCC TTAACTCATC TGTTATCCTG CTAGCTGTAG AAATGTATCC

TGATAAACAT TAAACACTGT AATCTTAAAA GTGTAATTGT GTGACTTTTT

CAGAGTTGCT TTAAAGTACC TGTAGTGAGA AACTGATTTA TGATCACTTG

GAAGATTTGT ATAGTTTTAT AAAACTCAGT TAAAATGTCT GTTTCAATGA

CCTGTATTTT GCCAGACTTA AATCACAGAT GGGTATTAAA CTTGTCAGAA

TTTCTTTGTC ATTCAAGCCT GTGAATAAAA ACCCTGTATG GCACTTATTA

TGAGGCTATT AAAAGAATCC AAATTCAAAC TAAATTAGCT CTGATACTTA

TTTATATAAA CTGCTTCAGT GGAACAGATT TAGTAATACT AACAGTGATA

GCATTTTATT TTGAAAGTGT TTTGAGACCA TCAAAATGCA TACTTTAAAA

CAGCAGGTCT TTTAGCTAAA ACTAACACAA CTCTGCTTAG ACAAATAGGC

TGTCCTTTGA AGCTT   SEQ ID NO: 1
```

Fig. 2-3

```
  1 CCGCCGGCGC GCAGGAGCGG CACTCGTGGC TGTGGTGGCT TCGGCAGCGG

51 CTTCAGCAGA TCGGCGGCAT CAGCGGTACG ACCAGCACTA GCAGC    ATG
                                                         met
 99 TTG AGC CGG GCA GTG TGC GGC ACC AGC AGG CAG CTG GCT CCG
    leu ser arg ala val cys gly thr ser arg gln leu ala pro 141 GCT TTG GGG TAT CTG GGC TCC AGG CAG AAG CAC AGC CTC CCC
    ala leu gly tyr leu gly ser arg gln lys his ser leu pro 183 GAC CTG CCC TAC GAC TAC GGC GCC CTG GAA CCT CAC ATC AAC
    asp leu pro tyr asp tyr gly ala leu glu pro his ile asn 225 GCG CAG ATC ATG CAG CTG CAC CAC AGC AAG CAC CAC GCG GCC
    ala gln ile met gln leu his his ser lys his his ala ala 267 TAC GTG AAC AAC CTG AAC GTC ACC GAG GAG AAG TAC CAG GAG
    tyr val asn asn leu asn val thr glu glu lys tyr gln glu 309 GCG TTG GCA AAG GGA GAT GTT ACA GCC CAG ACA GCT CTT CAG
    ala leu ala lys gly asp val thr ala gln thr ala leu gln 351 CCT GCA CTG AAG TTC AAT GGT GGT GGT CAT ATC AAT CAT AGC
    pro ala leu lys phe asn gly gly gly his ile asn his ser 393 ATT TTC TGG ACA AAC CTC AGC CCT AAC GGT GGT GGA GAA CCC
    ile phe trp thr asn leu ser pro asn gly gly gly glu pro 435 AAA GGG GAG TTG CTG GAA GCC ATC AAA CGT GAC TTT GGT TCC
    lys gly glu leu leu glu ala ile lys arg asp phe gly ser 477 TTT GAC AAG TTT AAG GAG AAG CTG ACG GCT GCA TCT GTT GGT
    phe asp lys phe lys glu lys leu thr ala ala ser val gly 519 GTC CAA GGC TCA GGT TGG GGT TGG CTT GGT TTC AAT AAG GAA
    val gln gly ser gly trp gly trp leu gly phe asn lys glu 561 CGG GGA CAC TTA CAA ATT GCT GCT TGT CCA AAT CAG GAT CCA
    arg gly his leu gln ile ala ala cys pro asn gln asp pro 603 CTG CAA GGA ACA ACA GGC CTT ATT CCA CTG CTG GGG ATT GAT
    leu gln gly thr thr gly leu ile pro leu leu gly ile asp 645 GTG TGG GAG CAC GCT TAC TAC CTT CAG TAT AAA AAT GTC AGG
    val trp glu his ala tyr tyr leu gln tyr lys asn val arg 687 CCT GAT TAT CTA AAA GCT ATT TGG AAT GTA ATC AAC TGG GAG
    pro asp tyr leu lys ala ile trp asn val ile asn trp glu 729 AAT GTA ACT GAA AGA TAC ATG GCT TGC AAA AAG TAA  ACCACG
    asn val thr glu arg tyr met ala cys lys lys

771 ATCGTTATGC TGAGTATGTT AAGCTCTTTA TGACTGTTTT TGTAGTGGTA
```

Fig. 3-1

```
821 TAGAGTACTG CAGAATACAG TAAGCTGCTC TATTGTAGCA TTTCTTGATG
871 TTGCTTAGTC ACTTATTTCA TAAACAACTT AATGTTCTGA ATAATTTCTT
921 ACTAAACATT TTGTTATTGG GCAAGTGATT GAAAATAGTA AATGCTTTGT
971 GTGATTG    SEQ ID NO: 2
```

Fig. 3-2

```
  1 CTGGGTGCAG CTCTCTTTTC AGGAGAGAAA GCTCTCTTGG AGGAGCTOGA

51 AAGGTGCCCG ACTCCAGCC    ATG CTG GCG CTA CTG TGT TCC TGC
                            met leu ala leu leu cys ser cys 94 CTG C.C CTG GCA GCC GGT GCC TCG GAC GCC TGG ACG GGC GAG
    leu leu leu ala ala gly ala ser asp ala trp thr gly glu 136 GAC TCG GCG GAG CCC AAC TCT GAC TCG GCG GAG TGG ATC CGA
    asp ser ala glu pro asn ser asp ser ala glu trp ile arg 178 GAC ATG TAC GCC AAG GTC ACG GAG ATC TGG CAG GAG GTC ATG
    asp met tyr ala lys val thr glu ile trp gln glu val met 220 CAG CGG CGG GAC GAC GAC GGC ACG CTC CAC GCC GCC TGC CAG
    gln arg arg asp asp asp gly thr leu his ala ala cys gln 262 GTG CAG CCG TCG GCC ACG CTG GAC GCC GCG CAG CCC CGG GTG
    val gln pro ser ala thr leu asp ala ala gln pro arg val 304 ACC GGC GTC GTC CTC TTC CGG CAG CTT GCG CCC CGC GCC AAG
    thr gly val val leu phe arg gln leu ala pro arg ala lys 346 CTC GAC GCC TTC TTC GCC CTG GAG GGC TTC CCG ACC GAG CCG
    leu asp ala phe phe ala leu glu gly phe pro thr glu pro 388 AAC AGC TCC AGC CGC GCC ATC CAC GTG CAC CAG TTC GGG GAC
    asn ser ser ser arg ala ile his val his gln phe gly asp 430 CTG AGC CAG GGC TGC GAG TCC ACC GGG CCC CAC TAC AAC CCG
    leu ser gln gly cys glu ser thr gly pro his tyr asn pro 472 CTG GCC GTG CCG CAC CCG CAG CAC CCG GGC GAC TTC GGC AAC
    leu ala val pro his pro gln his pro gly asp phe gly asn 514 TTC GCG GTC CGC GAC GGC AGC CTC TGG AGG TAC CGC GCC GGC
    phe ala val arg asp gly ser leu trp arg tyr arg ala gly 556 CTG GCC GCC TCG CTC GCG GGC CCG CAC TCC ATC GTG GGC CGG
    leu ala ala ser leu ala gly pro his ser ile val gly arg 598 GCC GTG GTC GTC CAC GCT GGC GAG GAC GAC CTG GGC CGC GGC
    ala val val val his ala gly glu asp asp leu gly arg gly 640 GGC AAC CAG GCC AGC GTG GAG AAC GGG AAC GCG GGC CGG CGG
    gly asn gln ala ser val glu asn gly asn ala gly arg arg 682 CTG GCC TGC TGC GTG GTG GGC GTG TGC GGG CCC GGG CTC TGG
    leu ala cys cys val val gly val cys gly pro gly leu trp 724 GAG CGC CAG GCG CGG GAG CAC TCA GAG CGC AAG AAG CGG CGG
    glu arg gln ala arg glu his ser glu arg lys lys arg arg 766 CGC GAG AGC GAG TGC AAG GCC GCC TGA GCGCGGCC CCCACCCGGC
    arg glu ser glu cys lys ala ala
```

Fig. 4-1

```
 811 GGCGGCCAGG GACCCCCGAG GCCCCCCTCT GCCTTTCAGC TTCTCCTCTG
 861 CTCCAACAGA CACCTTCCAC TCTGAGGTCT CACCTTCGCC TCTGCTGAAG
 911 TCTCCCCGCA GCCCTCTCCA CCCAGAGGTC TCCCTATACC GAGACCCACC
 961 ATCCTTCCAT CCTGAGGACC GCCCAACCC TCGGAGCCCC CCACTCAGTA
1011 GGTCTGAAGG CCTCCATTTG TACCGAAACA CCCCGCTCAC GCTGACAGCC
1061 TCCTAGGCTC CCTGAGGTAC CTTTCCACCC AGACCCTCCT TCCCCACCCC
1111 ATAAGCCCTG AGACTCCCGC CTTTGACCTG ACGATCTTCC CCCTTCCCGC
1161 CTTCAGGTTC CTCCTAGGCG CTCAGAGGCC GCTCTGGGGG GTTGCCTCGA
1211 GTCCCCCCAC CCCTCCCCAC CCACCACCGC TCCCGCGGCA AGCCAGCCCG
1261 TGCAACGGAA GCCAGGCCAA CTGCCCGCG TCTTCAGCTG TTTCGCATCC
1311 ACCGCCACCC CACTGAGAGC TGCTCCTTTG GGGGAATGTT TGGCAACCTT
1361 TGTGTTACAG ATTAAAAATT CAGCAATTC   SEQ ID NO: 3
```

Fig. 4-2

Exon 1
    5' ATA AAG TAG TCG CGG AGA CGG 3'    SEQ ID NO: 4
    5' GCC TTC TGC TCG AAA TTG ATG 3'    SEQ ID NO: 5

Exon 2
    5' ACT CTC TCC AAC TTT GCA CTT 3'    SEQ ID NO: 6
    5' CCC ACC TGC TGT ATT ATC TCC 3'    SEQ ID NO: 7

Exon 3
    5' GAA TGT ATT TGG GAA CTT TAA TTC 3'    SEQ ID NO: 8
    5' TAG ATG AGT CAG CAA GTT CAA AAG 3'    SEQ ID NO: 9

Exon 4
    5' CAT ATA GGC ATG TTG GAG ACT 3'    SEQ ID NO: 10
    5' GAA AGA TAC ATG ACT GTA CTG 3'    SEQ ID NO: 11

Exon 5
    5' GTA TTG TTG GGA GGA GGT AGT GAT 3'    SEQ ID NO: 12
    5' GCA GGA TAA CAG ATG AGT TAA GGG 3'    SEQ ID NO: 13

Fig. 5

SOD-2
    5' GCA ACA TCA AGA AAT GCT AC 3'    SEQ ID NO: 14
    5' GGC ACT CGT GGC TGT GGT GGC TTC 3'    SEQ ID NO: 15

SOD-3
    5' CAC AAA GGT AGC CAA ACA TTC 3'    SEQ ID NO: 16
    5' GTG CAG CTC TCT TTT CAG GAG 3'    SEQ ID NO: 17

Fig. 6

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 2800 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: Xaa at position 5 is Ala or Val. Xaa at position 38 is Gly or Arg. Xaa at position 39 is Leu or Val. Xaa at position 42 is Gly, Ser or Asp. Xaa at position 44 is His or Arg. Xaa at position 86 is Gly or Arg. Xaa at position 94 is Gly, Cys or Ala. Xaa at position 101 is Gly or Glu. Xaa at position 107 is Leu or Val. Xaa at position 114 is Ile or Thr. Xaa at position 145 is Leu or Ser. Xaa at position 146 is Ala or Thr.

(xi) SEQUENCE DESCRIPTION: SEQ ID NO:1:

```
GAATTCTGCC AACCAAATAA GAAACTCTAT ACTAAGGACT AAGAAAATTG CAGGGGAAGA    60
AAAGGTAAGT CCCGGGATTG AGGTGTAGCG ACTTTCTATA CCCTCAGAAA ACTAAAAAAC   120
AAGACAAAAA AATGAAAACT ACAAAAGCAT CCATCTTGGG GCGTCCCAAT TGCTGAGTAA   180
CAAATGAGAC GCTGTGGCCA AACTCACGTC ATAACTAATG ACATTTCTAG ACAAAGTGAC   240
TTCAGATTTT CAAAGCGTAC CCTGTTTACA TCATTTTGCC AATTTCGCGT ACTGCAACCG   300
GCGGGCCACG CCCCCGTGAA AAGAAGGTTG TTTTCTCCAC ATTTCGGGGT TCTGGACGTT   360
TCCCGGCTGC GGGGCGGGGG GAGTCTCCGG CGCACGCGGC CCCTTGGCCC CGCCCCAGT    420
CATTCCCGGC CACTCGCGAC CCGAGGCTGC CGCAGGGGGC GGGCTGAGCG CGTGCGAGGC   480
GATTGGTTTG GGGCCAGAGT GGGCGAGGCG CGGAGGTCTG GCCTATAAAG TAGTCGCGGA   540
GACGGGGTGC TGGTTTGCGT CGTAGTCTCC TGCAGCGTCT GGGGTTTCCG TTGCAGTCCT   600
CGGAACCAGG ACCTCGGCGT GGCCTAGCGA GTT ATG GCG ACG AAG GYC GTG TGC   654
```

```
                                    Met Ala Thr Lys Xaa Val Cys
                                     1               5
GTG CTG AAG GGC GAC GGC CCA GTG CAG GGC ATC ATC AAT TTC GAG CAG           702
Val Leu Lys Gly Asp Gly Pro Val Gln Gly Ile Ile Asn Phe Glu Gln
         10                  15                  20

AAG G CAAGGGCTGG GACGGGAGGC TTGTGGTTGC GAGGCCGCTC CCGACCCGCT              756
Lys

CGTCCCCCCG CGACCCTTTG CATGGACGGG TCGCCCGCCA GGGCCTAGAG CAGGTTAAGC         816

AGCTTGCTGG AGGTTCACTG GCTAGAAAGT GGTCAGCCTG GGATTTGGAC ACAGATTTTT         876

CCACTCCCAA GTCTGGCTGC TTTTTACTTC ACTGTGAGGG GTAAAGGTAA ATCAGCTGTT         936

TTCTTTGTTC AGAAACTCTC TCCAACTTTG CACTTTTCTT AAAG GAA AGT AAT GGA          992
                                                 Glu Ser Asn Gly
                                                  1

CCA GTG AAG GTG TGG GGA AGC ATT AAA NGA STG ACT GAA RRC CTG CRT          1040
Pro Val Lys Val Trp Gly Ser Ile Lys Xaa Xaa Thr Glu Xaa Leu Xaa
 5               10                  15                  20

GGA TTC CAT GTT CAT GAG TTT GGA GAT AAT ACA GCA G GTCGGGTGTT             1087
Gly Phe His Val His Glu Phe Gly Asp Asn Thr Ala
             25                  30

GTGTTTCTTT TTAGAATGTA TTTGGGAACT TTAATTCATA ATTTAGCTTT TTTTCTTCT         1147

TCTTATAAAT A GGC TGT ACC AGT GCA GGT CCT CAC TTT AAT CCT CTA TCC         1197
             Gly Cys Thr Ser Ala Gly Pro His Phe Asn Pro Leu Ser
              1               5                   10

AGA AAA CAC GGT GGG CCA AAG GAT GAA GAG AGG T AACAAGATGC                 1241
Arg Lys His Gly Gly Pro Lys Asp Glu Glu Arg
         15                  20

TTAACTCTTG TAATAATGGC CGATCATGGT TCTGGAGTTC ATATGGTATA CTACTTGTAA        1301

ATATGTGCTA AGATAATTCC GTGTTTCCCC CACCTTTGCT TTTGAACTTG CTGACTCATC        1361

TAAACCCTGC TCCCAAATGC TGGAATGCTT TTACTTCCTG GGCTTAAAGG AATTGACAAA        1421

TGGGCACTTA AAACGATTTG GTTTTGTAGC ATTTGATTGA ATATAGAACT AATACAAGTG        1481

CCAAAGGGGA ACTAATACAG GAAATGTTCA TGAACAGTAC TGTCAACCAC TAGCAAAATC        1541

AATCATCATT GTACTTCTGA AATCAGGTGC AGCCCCATCT TTCTTCCCAG AGCATTAGTG        1601

TGTAGACGTG AAGCCTTGTT TGAAGAGCTG TATTTAGAAT GCCTAGCTAC TTGTTTGCAA        1661

ATTTGTGTCC TACTCAGTCA AGTTTTAATT TAGCTCATGA ACTACCTTGA TGTTTAGTGG        1721

CATCAGCCCT AATCCATCTG ATGCTTTTTC ATTATTAGG CAT GTT GGA GAC TTG          1775
                                             His Val Gly Asp Leu
                                              1               5

SGC AAT GTG ACT GCT GAC AAA GAT KST GTG GCC GAT GTG TCT ATT GRA         1823
Xaa Asn Val Thr Ala Asp Lys Asp Xaa Val Ala Asp Val Ser Ile Xaa
         10                  15                  20

GAT TCT GTG ATC TCA STC TCA GGA GAC CAT TGC ATC AYT GGC CGC ACA         1871
Asp Ser Val Ile Ser Xaa Ser Gly Asp His Cys Ile Xaa Gly Arg Thr
         25                  30                  35

CTG GTG G TAAGTTTTCA TAAAAGGATA TGCATAAAAC TTCTTCTAAC ATACAGTCAT        1928
Leu Val

GTATCTTTTC ACTTTGATTG TTAGTCGCGG TTTCTAAGAT CCAGATAAAC TGTGAAAAAG       1988

CTTTGAGTAG TAGTTTCTAC TTTTAAACTA CTAAATATTA GTATATCTCT CTACTAGGAT       2048

TAATGTTATT TTTCTAATAT TATGAGGTTC TTAAACATCT TTTGGGTATT GTTGGGAGGA       2108

GGTAGTGATT ACTTGACAGC CCAAAGTTAT CTTCTTAAAA TTTTTTACAG GTC CAT          2164
                                                          Val His
                                                           1

GAA AAA GCA GAT GAC TTG GGC AAA GGT GGA AAT GAA GAA AGT ACA AAG         2212
```

```
Glu  Lys  Ala  Asp  Asp  Leu  Gly  Lys  Gly  Gly  Asn  Glu  Glu  Ser  Thr  Lys
          5                        10                       15

ACA  GGA  AAC  GAT  GGA  AGT  CGT  TYG  RCT  TGT  GGT  GTA  ATT  GGG  ATC  GCC         2260
Thr  Gly  Asn  Asp  Gly  Ser  Arg  Xaa  Xaa  Cys  Gly  Val  Ile  Gly  Ile  Ala
          20                       25                       30

CAA  T      AAACATTCCC   TTGGATGTAG   TCTGAGGCCC   CTTAACTCAT   CTGTTATCCT              2314
Gln
35

GCTAGCTGTA   GAAATGTATC   CTGATAAACA   TTAAACACTG   TAATCTTAAA   AGTGTAATTG             2374

TGTGACTTTT   TCAGAGTTGC   TTTAAAGTAC   CTGTAGTGAG   AAACTGATTT   ATGATCACTT             2434

GGAAGATTTG   TATAGTTTTA   TAAAACTCAG   TTAAAATGTC   TGTTTCAATG   ACCTGTATTT             2494

TGCCAGACTT   AAATCACAGA   TGGGTATTAA   ACTTGTCAGA   ATTTCTTTGT   CATTCAAGCC             2554

TGTGAATAAA   AACCCTGTAT   GGCACTTATT   ATGAGGCTAT   TAAAAGAATC   CAAATTCAAA             2614

CTAAATTAGC   TCTGATACTT   ATTTATATAA   ACTGCTTCAG   TGGAACAGAT   TTAGTAATAC             2674

TAACAGTGAT   AGCATTTTAT   TTTGAAAGTG   TTTTGAGACC   ATCAAAATGC   ATACTTTAAA             2734

ACAGCAGGTC   TTTTAGCTAA   AACTAACACA   ACTCTGCTTA   GACAAATAGG   CTGTCCTTTG             2794

AAGCTT                                                                                  2800
```

( 2 ) INFORMATION FOR SEQ ID NO:2:

( i ) SEQUENCE CHARACTERISTICS:
        ( A ) LENGTH: 977 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
CCGCCGGCGC   GCAGGAGCGG   CACTCGTGGC   TGTGGTGGCT   TCGGCAGCGG   CTTCAGCAGA              60

TCGGCGGCAT   CAGCGGTACG   ACCAGCACTA   GCAGC  ATG  TTG  AGC  CGG  GCA  GTG              113
                                              Met  Leu  Ser  Arg  Ala  Val
                                                                       40

TGC  GGC  ACC  AGC  AGG  CAG  CTG  GCT  CCG  GCT  TTG  GGG  TAT  CTG  GGC  TCC         161
Cys  Gly  Thr  Ser  Arg  Gln  Leu  Ala  Pro  Ala  Leu  Gly  Tyr  Leu  Gly  Ser
               45                       50                       55

AGG  CAG  AAG  CAC  AGC  CTC  CCC  GAC  CTG  CCC  TAC  GAC  TAC  GGC  GCC  CTG         209
Arg  Gln  Lys  His  Ser  Leu  Pro  Asp  Leu  Pro  Tyr  Asp  Tyr  Gly  Ala  Leu
               60                       65                       70

GAA  CCT  CAC  ATC  AAC  GCG  CAG  ATC  ATG  CAG  CTG  CAC  CAC  AGC  AAG  CAC         257
Glu  Pro  His  Ile  Asn  Ala  Gln  Ile  Met  Gln  Leu  His  His  Ser  Lys  His
     75                       80                       85

CAC  GCG  GCC  TAC  GTG  AAC  AAC  CTG  AAC  GTC  ACC  GAG  GAG  AAG  TAC  CAG         305
His  Ala  Ala  Tyr  Val  Asn  Asn  Leu  Asn  Val  Thr  Glu  Glu  Lys  Tyr  Gln
90                       95                       100                      105

GAG  GCG  TTG  GCA  AAG  GGA  GAT  GTT  ACA  GCC  CAG  ACA  GCT  CTT  CAG  CCT         353
Glu  Ala  Leu  Ala  Lys  Gly  Asp  Val  Thr  Ala  Gln  Thr  Ala  Leu  Gln  Pro
               110                      115                      120

GCA  CTG  AAG  TTC  AAT  GGT  GGT  GGT  CAT  ATC  AAT  CAT  AGC  ATT  TTC  TGG         401
Ala  Leu  Lys  Phe  Asn  Gly  Gly  Gly  His  Ile  Asn  His  Ser  Ile  Phe  Trp
               125                      130                      135

ACA  AAC  CTC  AGC  CCT  AAC  GGT  GGT  GGA  GAA  CCC  AAA  GGG  GAG  TTG  CTG         449
Thr  Asn  Leu  Ser  Pro  Asn  Gly  Gly  Gly  Glu  Pro  Lys  Gly  Glu  Leu  Leu
               140                      145                      150

GAA  GCC  ATC  AAA  CGT  GAC  TTT  GGT  TCC  TTT  GAC  AAG  TTT  AAG  GAG  AAG         497
Glu  Ala  Ile  Lys  Arg  Asp  Phe  Gly  Ser  Phe  Asp  Lys  Phe  Lys  Glu  Lys
               155                      160                      165
```

| | | | | | | | | | | | | | | | | |
|---|---|---|---|---|---|---|---|---|---|---|---|---|---|---|---|---|
|CTG|ACG|GCT|GCA|TCT|GTT|GGT|GTC|CAA|GGC|TCA|GGT|TGG|GGT|TGG|CTT|545|
|Leu|Thr|Ala|Ala|Ser|Val|Gly|Val|Gln|Gly|Ser|Gly|Trp|Gly|Trp|Leu||
|170| | | |175| | | |180| | | | | |185| | |
|GGT|TTC|AAT|AAG|GAA|CGG|GGA|CAC|TTA|CAA|ATT|GCT|GCT|TGT|CCA|AAT|593|
|Gly|Phe|Asn|Lys|Glu|Arg|Gly|His|Leu|Gln|Ile|Ala|Ala|Cys|Pro|Asn||
| | | |190| | | |195| | | | | |200| | | |
|CAG|GAT|CCA|CTG|CAA|GGA|ACA|ACA|GGC|CTT|ATT|CCA|CTG|CTG|GGG|ATT|641|
|Gln|Asp|Pro|Leu|Gln|Gly|Thr|Thr|Gly|Leu|Ile|Pro|Leu|Leu|Gly|Ile||
| | |205| | | | |210| | | | |215| | | | |
|GAT|GTG|TGG|GAG|CAC|GCT|TAC|TAC|CTT|CAG|TAT|AAA|AAT|GTC|AGG|CCT|689|
|Asp|Val|Trp|Glu|His|Ala|Tyr|Tyr|Leu|Gln|Tyr|Lys|Asn|Val|Arg|Pro||
| | |220| | | | |225| | | |230| | | | | |
|GAT|TAT|CTA|AAA|GCT|ATT|TGG|AAT|GTA|ATC|AAC|TGG|GAG|AAT|GTA|ACT|737|
|Asp|Tyr|Leu|Lys|Ala|Ile|Trp|Asn|Val|Ile|Asn|Trp|Glu|Asn|Val|Thr||
| |235| | | | |240| | | |245| | | | | | |
|GAA|AGA|TAC|ATG|GCT|TGC|AAA|AAG|T|AAACCACGAT|CGTTATGCTG| | | | | |782|
|Glu|Arg|Tyr|Met|Ala|Cys|Lys|Lys| | | | | | | | | |
|250| | | | |255| | | | | | | | | | | |

| | | | | |
|---|---|---|---|---|
|AGTATGTTAA|GCTCTTTATG|ACTGTTTTTG|TAGTGGTATA|GAGTACTGCA GAATACAGTA|842|
|AGCTGCTCTA|TTGTAGCATT|TCTTGATGTT|GCTTAGTCAC|TTATTTCATA AACAACTTAA|902|
|TGTTCTGAAT|AATTTCTTAC|TAAACATTTT|GTTATTGGGC|AAGTGATTGA AAATAGTAAA|962|
|TGCTTTGTGT|GATTG| | | |977|

( 2 ) INFORMATION FOR SEQ ID NO:3:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

| | | | | | | | | | | | | | | | | |
|---|---|---|---|---|---|---|---|---|---|---|---|---|---|---|---|---|
|CTGGGTGCAG|CTCTCTTTTC|AGGAGAGAAA|GCTCTCTTGG|AGGAGCTGGA|AAGGTGCCCG| | | | | | | | | | |60|
|ACTCCAGCC|ATG|CTG|GCG|CTA|CTG|TGT|TCC|TGC|CTG|CTC|CTG|GCA|GCC| | |108|
| |Met|Leu|Ala|Leu|Leu|Cys|Ser|Cys|Leu|Leu|Leu|Ala|Ala| | | |
| | |225| | | | |230| | | | |235| | | | |
|GGT|GCC|TCG|GAC|GCC|TGG|ACG|GGC|GAG|GAC|TCG|GCG|GAG|CCC|AAC|TCT|156|
|Gly|Ala|Ser|Asp|Ala|Trp|Thr|Gly|Glu|Asp|Ser|Ala|Glu|Pro|Asn|Ser||
| | | |240| | | | |245| | | | |250| | | |
|GAC|TCG|GCG|GAG|TGG|ATC|CGA|GAC|ATG|TAC|GCC|AAG|GTC|ACG|GAG|ATC|204|
|Asp|Ser|Ala|Glu|Trp|Ile|Arg|Asp|Met|Tyr|Ala|Lys|Val|Thr|Glu|Ile||
| | |255| | | | |260| | | | |265| | | | |
|TGG|CAG|GAG|GTC|ATG|CAG|CGG|CGG|GAC|GAC|GAC|GGC|ACG|CTC|CAC|GCC|252|
|Trp|Gln|Glu|Val|Met|Gln|Arg|Arg|Asp|Asp|Asp|Gly|Thr|Leu|His|Ala||
| |270| | | | |275| | | | |280| | | | | |
|GCC|TGC|CAG|GTG|CAG|CCG|TCG|GCC|ACG|CTG|GAC|GCC|GCG|CAG|CCC|CGG|300|
|Ala|Cys|Gln|Val|Gln|Pro|Ser|Ala|Thr|Leu|Asp|Ala|Ala|Gln|Pro|Arg||
| |285| | | | |290| | | | |295| | | | | |
|GTG|ACC|GGC|GTC|GTC|CTC|TTC|CGG|CAG|CTT|GCG|CCC|CGC|GCC|AAG|CTC|348|
|Val|Thr|Gly|Val|Val|Leu|Phe|Arg|Gln|Leu|Ala|Pro|Arg|Ala|Lys|Leu||
|300| | | | |305| | | | |310| | | | |315| |
|GAC|GCC|TTC|TTC|GCC|CTG|GAG|GGC|TTC|CCG|ACC|GAG|CCG|AAC|AGC|TCC|396|
|Asp|Ala|Phe|Phe|Ala|Leu|Glu|Gly|Phe|Pro|Thr|Glu|Pro|Asn|Ser|Ser||
| | | |320| | | | |325| | | | |330| | | |
|AGC|CGC|GCC|ATC|CAC|GTG|CAC|CAG|TTC|GGG|GAC|CTG|AGC|CAG|GGC|TGC|444|
|Ser|Arg|Ala|Ile|His|Val|His|Gln|Phe|Gly|Asp|Leu|Ser|Gln|Gly|Cys||
| | | |335| | | | |340| | | | |345| | | |
|GAG|TCC|ACC|GGG|CCC|CAC|TAC|AAC|AAG|CTG|GCC|GTG|CCG|CAC|CCG|CAG|492|

```
Glu  Ser  Thr  Gly  Pro  His  Tyr  Asn  Lys  Leu  Ala  Val  Pro  His  Pro  Gln
          350                           355                      360

CAC  CCG  GGC  GAC  TTC  GGC  AAC  TTC  GCG  GTC  CGC  GAC  GGC  AGC  CTC  TGG        540
His  Pro  Gly  Asp  Phe  Gly  Asn  Phe  Ala  Val  Arg  Asp  Gly  Ser  Leu  Trp
     365                           370                      375

AGG  TAC  CGC  GCC  GGC  CTG  GCC  GCC  TCG  CTC  GCG  GGC  CCG  CAC  TCC  ATC        588
Arg  Tyr  Arg  Ala  Gly  Leu  Ala  Ala  Ser  Leu  Ala  Gly  Pro  His  Ser  Ile
380                      385                      390                      395

GTG  GGC  CGG  GCC  GTG  GTC  GTC  CAC  GCT  GGC  GAG  GAC  GAC  CTG  GGC  CGC        636
Val  Gly  Arg  Ala  Val  Val  Val  His  Ala  Gly  Glu  Asp  Asp  Leu  Gly  Arg
                    400                      405                      410

GGC  GGC  AAC  CAG  GCC  AGC  GTG  GAG  AAC  GGG  AAC  GCG  GGC  CGG  CGG  CTG        684
Gly  Gly  Asn  Gln  Ala  Ser  Val  Glu  Asn  Gly  Asn  Ala  Gly  Arg  Arg  Leu
               415                      420                      425

GCC  TGC  TGC  GTG  GTG  GGC  GTG  TGC  GGG  CCC  GGG  CTC  TGG  GAG  CGC  CAG        732
Ala  Cys  Cys  Val  Val  Gly  Val  Cys  Gly  Pro  Gly  Leu  Trp  Glu  Arg  Gln
          430                      435                      440

GCG  CGG  GAG  CAC  TCA  GAG  CGC  AAG  AAG  CGG  CGG  CGC  GAG  AGC  GAG  TGC        780
Ala  Arg  Glu  His  Ser  Glu  Arg  Lys  Lys  Arg  Arg  Arg  Glu  Ser  Glu  Cys
     445                      450                      455

AAG  GCC  GCC  T GAGCGCGGCC  CCCACCCGGC  GGCGGCCAGG  GACCCCGAG                         830
Lys  Ala  Ala
460

GCCCCCTCT  GCCTTTGAGC  TTCTCCTCTG  CTCCAACAGA  CACCTTCCAC  TCTGAGGTCT                  890

CACCTTCGCC  TCTGCTGAAG  TCTCCCCGCA  GCCCTCTCCA  CCCAGAGGTC  TCCCTATACC                 950

GAGACCCACC  ATCCTTCCAT  CCTGAGGACC  GCCCCAACCC  TCGGAGCCCC  CCACTCAGTA                1010

GGTCTGAAGG  CCTCCATTTG  TACCGAAACA  CCCCGCTCAC  GCTGACAGCC  TCCTAGGCTC                1070

CCTGAGGTAC  CTTTCCACCC  AGACCCTCCT  TCCCCACCCC  ATAAGCCCTG  AGACTCCGC                 1130

CTTTGACCTG  ACGATCTTCC  CCCTTCCCGC  CTTCAGGTTC  CTCCTAGGCG  CTCAGAGGCC                1190

GCTCTGGGGG  GTTGCCTCGA  GTCCCCCAC   CCCTCCCAC   CCACCACCGC  TCCCGCGGCA                1250

AGCCAGCCCG  TGCAACGGAA  GCCAGGCCAA  CTGCCCCGCG  TCTTCAGCTG  TTTCGCATCC                1310

ACCGCCACCC  CACTGAGAGC  TGCTCCTTTG  GGGGAATGTT  TGGCAACCTT  TGTGTTACAG                1370

ATTAAAAATT  CAGCAATTC                                                                 1389
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ATAAAGTAGT  CGCGGAGACG  G                                                               21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GCCTTCTGCT  CGAAATTGAT  G                                                               21

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:6:

ACTCTCTCCA ACTTTGCACT T    21

( 2 ) INFORMATION FOR SEQ ID NO:7:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

CCCACCTGCT GTATTATCTC C    21

( 2 ) INFORMATION FOR SEQ ID NO:8:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

TTCAGAAACT CTCTCCAACT T    21

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

CGTTTAGGGG CTACTCTACT GT    22

( 2 ) INFORMATION FOR SEQ ID NO:10:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

CATATAGGCA TGTTGGAGAC T    21

( 2 ) INFORMATION FOR SEQ ID NO:11:

( i ) SEQUENCE CHARACTERISTICS:

(A) LENGTH: 24 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:11:

TCTTAGAATT CGCGACTAAC AATC                      24

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:12:

CATCAGCCCT AATCCATCTG A                         21

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:13:

CGCGACTAAC AATCAAAGTG A                         21

(2) INFORMATION FOR SEQ ID NO:14:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:14:

GAATGTATTT GGGAACTTTA ATTC                      24

(2) INFORMATION FOR SEQ ID NO:15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA (x i) SEQUENCE DESCRIPTION: SEQ ID NO:15:

TAGATGAGTC AGCAAGTTCA AAAG                      24

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear ( i i ) MOLECULE TYPE: DNA ( x i ) SEQUENCE DESCRIPTION: SEQ ID NO:16:

GAAAGATACA TGACTGTACT G                                                        21

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GTATTGTTGG GAGGAGGTAG TGAT                                                     24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GCAGGATAAC AGATGAGTTA AGGG                                                     24

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

GCAACATCAA GAAATGCTAC                                                          20

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GGCACTCGTG GCTGTGGTGG CTTC                                                     24

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CACAAAGGTA GCCAAACATT C                                                        21

( 2 ) INFORMATION FOR SEQ ID NO:22:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:22:

GTGCAGCTCT CTTTTCAGGA G        21

( 2 ) INFORMATION FOR SEQ ID NO:23:

( i ) SEQUENCE CHARACTERISTICS:
      ( A ) LENGTH: 32 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:23:

```
Glu Ser Asn Gly Pro Val Lys Val Trp Gly Ser Ile Lys Gly Leu Thr
 1               5                  10                 15
Glu Gly Leu His Gly Phe His Val His Glu Phe Gly Asp Asn Thr Ala
                20                  25                 30
```

( 2 ) INFORMATION FOR SEQ ID NO:24:

( i ) SEQUENCE CHARACTERISTICS:
      ( A ) LENGTH: 29 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:24:

```
Gly Asp Thr Val Val Val Thr Gly Ser Ile Thr Gly Leu Thr Glu Gly
 1               5                  10                 15
His Gly Phe His Val His Gln Phe Gly Asp Asn Thr Gln
                20                  25
```

( 2 ) INFORMATION FOR SEQ ID NO:25:

( i ) SEQUENCE CHARACTERISTICS:
      ( A ) LENGTH: 31 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:25:

```
Gly Glu Lys Thr Val Leu Val Thr Gly Thr Ile Lys Gly Leu Ala Glu
 1               5                  10                 15
Gly Asp His Gly Phe His Val His Gln Phe Gly Asp Asn Thr Gln
                20                  25                 30
```

( 2 ) INFORMATION FOR SEQ ID NO:26:

( i ) SEQUENCE CHARACTERISTICS:
      ( A ) LENGTH: 32 amino acids
      ( B ) TYPE: amino acid
      ( C ) STRANDEDNESS: Not Relevant (D) TOPOLOGY: linear (ii) MOLECULE TYPE: protein (xi) SEQUENCE DESCRIPTION: SEQ ID NO:26:

Ala Ser Gly Glu Pro Val Val Leu Ser Gly Gln Ile Thr Gly Leu Thr
1               5                   10                  15

Glu Gly Gln His Gly Phe His Val His Gln Tyr Gly Asp Asn Thr Gln
            20                  25                  30

(2) INFORMATION FOR SEQ ID NO:27:

(i) SEQUENCE CHARACTERISTICS:
      (A) LENGTH: 32 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:27:

Gly Asn Ala Asn Ala Val Gly Lys Gly Ile Ile Leu Lys Gly Leu Thr
1               5                   10                  15

Pro Gly Glu His Gly Phe His Val His Gly Phe Gly Asp Asn Thr Asn
            20                  25                  30

(2) INFORMATION FOR SEQ ID NO:28:

(i) SEQUENCE CHARACTERISTICS:
      (A) LENGTH: 32 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:28:

Ser Ser Gly Thr Pro Val Lys Val Ser Gly Glu Val Cys Gly Leu Ala
1               5                   10                  15

Lys Gly Leu His Gly Phe His Val His Glu Phe Gly Asp Asn Thr Asn
            20                  25                  30

(2) INFORMATION FOR SEQ ID NO:29:

(i) SEQUENCE CHARACTERISTICS:
      (A) LENGTH: 32 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:29:

Lys Glu Gly Leu Pro Thr Thr Val Thr Gly Glu Val Lys Gly Leu Thr
1               5                   10                  15

Pro Gly Leu His Gly Phe His Ile His Gln Tyr Gly Asp Thr Thr Asn
            20                  25                  30

(2) INFORMATION FOR SEQ ID NO:30:

(i) SEQUENCE CHARACTERISTICS:
      (A) LENGTH: 31 amino acids
      (B) TYPE: amino acid
      (C) STRANDEDNESS: Not Relevant
      (D) TOPOLOGY: linear (ii) MOLECULE TYPE: protein ( x i ) SEQUENCE DESCRIPTION: SEQ ID NO:30:

Gly Val Ala Pro Thr Thr Val Asn Gly Asn Ile Ser Gly Leu Lys Pro
1               5                   10                  15

Gly Leu His Gly Phe His Val His Ala Leu Gly Asp Thr Thr Asn
            20                  25                  30

( 2 ) INFORMATION FOR SEQ ID NO:31:

( i ) SEQUENCE CHARACTERISTICS:
        ( A ) LENGTH: 31 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:31:

Asp Asp Gly Pro Thr Thr Val Asn Val Arg Ile Ser Gly Leu Ala Pro
1               5                   10                  15

Gly Lys His Gly Phe His Leu His Glu Phe Gly Asp Thr Thr Asn
            20                  25                  30

( 2 ) INFORMATION FOR SEQ ID NO:32:

( i ) SEQUENCE CHARACTERISTICS:
        ( A ) LENGTH: 33 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:32:

Ser Glu Ser Glu Pro Thr Thr Val Ser Tyr Glu Ile Ala Gly Asn Ser
1               5                   10                  15

Pro Asn Ala Glu Arg Gly Phe His Ile His Glu Phe Gly Asp Ala Thr
            20                  25                  30

Asn ( 2 ) INFORMATION FOR SEQ ID NO:33:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:33:

His Val Gly Asp Leu Gly Asn Val Thr Ala Asp Lys Asp Gly Val Ala
1               5                   10                  15

Asp Val Ser Ile Glu Asp Ser Val Ile Ser Leu Ser Gly Asp His Cys
            20                  25                  30

Ile Ile Gly Arg Thr Leu Val
            35

( 2 ) INFORMATION FOR SEQ ID NO:34:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:34:

His Val Gly Asp Leu Gly Asn Val Thr Ala Asp Lys Asn Gly Val Ala
1               5                   10                  15

Ile Val Asp Ile Val Asp Pro Leu Ile Ser Leu Ser Gly Glu Tyr Ser
            20                  25                  30

Ile Ile Gly Arg Thr Met Val
        35

( 2 ) INFORMATION FOR SEQ ID NO:35:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:35:

His Val Gly Asp Leu Gly Asn Val Thr Ala Gly Lys Asp Gly Val Ala
1               5                   10                  15

Thr Val Tyr Ile Glu Asp Ser Val Ile Ala Leu Ser Gly Asp His Ser
            20                  25                  30

Ile Ile Gly Arg Thr Met Val
        35

( 2 ) INFORMATION FOR SEQ ID NO:36:

( i ) SEQUENCE CHARACTERISTICS:
        ( A ) LENGTH: 39 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:36:

His Val Gly Asp Leu Gly Asn Val Thr Ala Gly Lys Asp Gly Val Ala
1               5                   10                  15

Asn Val Ser Ile Glu Asp Arg Val Ile Ser Leu Ser Gly Glu His Ser
            20                  25                  30

Ile Ile Gly Arg Thr Met Val
        35

( 2 ) INFORMATION FOR SEQ ID NO:37:

( i ) SEQUENCE CHARACTERISTICS:
        ( A ) LENGTH: 38 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:37:

His Val Gly Asp Leu Gly Asn Val Thr Ala Asp Ala Asn Gly Val Ala
1               5                   10                  15

Lys Ile Asp Ile Thr Asp Lys Ile Ser Leu Thr Gly Pro Tyr Ser Ile
            20                  25                  30

Ile Gly Arg Thr Met Val
        35

( 2 ) INFORMATION FOR SEQ ID NO:38:

( i ) SEQUENCE CHARACTERISTICS:
  ( A ) LENGTH: 39 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:38:

His Leu Gly Asp Leu Gly Asn Ile Glu Ala Thr Gly Asp Cys Pro Thr
1               5                   10                  15

Lys Val Asn Ile Thr Asp Ser Lys Ile Thr Leu Phe Gly Ala Asp Ser
            20                  25                  30

Ile Ile Gly Arg Thr Val Val
            35

( 2 ) INFORMATION FOR SEQ ID NO:39:

( i ) SEQUENCE CHARACTERISTICS:
    ( A ) LENGTH: 39 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:39:

His Val Gly Asp Leu Gly Asn Ile Glu Ala Gly Ala Asp Gly Thr Ala
1               5                   10                  15

His Ile Ser Ile Ser Asp Gln His Ile Gln Leu Leu Gly Pro Asn Ser
            20                  25                  30

Ile Ile Gly Arg Ser Ile Val
            35

( 2 ) INFORMATION FOR SEQ ID NO:40:

( i ) SEQUENCE CHARACTERISTICS:
    ( A ) LENGTH: 39 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:40:

Glu Ala Gly Asp Leu Gly Asn Ile Thr Val Gly Glu Asp Gly Thr Ala
1               5                   10                  15

Ser Phe Thr Ile Thr Asp Lys Gln Ile Pro Leu Thr Gly Pro Gln Ser
            20                  25                  30

Ile Ile Gly Arg Ala Val Val
            35

( 2 ) INFORMATION FOR SEQ ID NO:41:

( i ) SEQUENCE CHARACTERISTICS:
    ( A ) LENGTH: 39 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:41:

His Ala Gly Asp Leu Gly Asn Ile Val Ala Asn Thr Asp Gly Val Ala
1               5                   10                  15

|   |   |   |   |   |   |   |   |   |   |   |   |   |   |   |
|---|---|---|---|---|---|---|---|---|---|---|---|---|---|---|
| Glu | Ala | Thr | Ile<br>20 | Val | Asp | Asn | Gln | Ile<br>25 | Pro | Leu | Thr | Gly | Pro<br>30 | Asn | Ser |
| Val | Val | Gly<br>35 | Arg | Ala | Leu | Val |

(2) INFORMATION FOR SEQ ID NO:42:

(i) SEQUENCE CHARACTERISTICS:
        (A) LENGTH: 39 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:42:

|   |   |   |   |   |   |   |   |   |   |   |   |   |   |   |
|---|---|---|---|---|---|---|---|---|---|---|---|---|---|---|
| His<br>1 | Val | Gly | Asp | Met<br>5 | Gly | Asn | Val | Lys | Thr<br>10 | Asp | Glu | Asn | Gly | Val<br>15 | Ala |
| Lys | Gly | Ser | Phe<br>20 | Lys | Asp | Ser | Leu | Ile<br>25 | Lys | Leu | Ile | Gly | Pro<br>30 | Thr | Ser |
| Val | Val | Gly<br>35 | Arg | Ser | Val | Val |

(2) INFORMATION FOR SEQ ID NO:43:

(i) SEQUENCE CHARACTERISTICS:
        (A) LENGTH: 154 amino acids
        (B) TYPE: amino acid
        (C) STRANDEDNESS: Not Relevant
        (D) TOPOLOGY: linear (ii) MOLECULE TYPE: protein (ix) FEATURE:
        (D) OTHER INFORMATION: Xaa at position 5 is Ala or Val. Xaa at position 38 is Gly or Arg. Xaa at position 39 is Leu or Val. Xaa at position 42 is Gly, Ser or Asp. Xaa at position 44 is His or Arg. Xaa at position 86 is Gly or Arg. Xaa at position 94 is Gly, Cys or Ala. Xaa at position 101 is Gly or Glu. Xaa at position 107 is Leu or Val. Xaa at position 114 is Ile or Thr. Xaa at position 145 is Leu or Ser. Xaa at position 146 is Ala or Thr.

(xi) SEQUENCE DESCRIPTION: SEQ ID NO:43:

|   |   |   |   |   |   |   |   |   |   |   |   |   |   |   |   |
|---|---|---|---|---|---|---|---|---|---|---|---|---|---|---|---|
| Met<br>1 | Ala | Thr | Lys | Xaa<br>5 | Val | Cys | Val | Leu | Lys<br>10 | Gly | Asp | Gly | Pro | Val<br>15 | Gln |
| Gly | Ile | Ile | Asn<br>20 | Phe | Glu | Gln | Lys | Ser<br>25 | Asn | Gly | Pro | Val | Lys<br>30 | Val |
| Trp | Gly | Ser<br>35 | Ile | Lys | Xaa | Xaa | Thr<br>40 | Glu | Xaa | Leu | Xaa | Gly<br>45 | Phe | His | Val |
| His | Glu<br>50 | Phe | Gly | Asp | Asn | Thr<br>55 | Ala | Gly | Cys | Thr | Ser<br>60 | Ala | Gly | Pro | His |
| Phe<br>65 | Asn | Pro | Leu | Ser | Arg<br>70 | Lys | His | Gly | Gly | Pro<br>75 | Lys | Asp | Glu | Glu | Arg<br>80 |
| His | Val | Gly | Asp | Leu<br>85 | Xaa | Asn | Val | Thr | Ala<br>90 | Asp | Lys | Asp | Xaa | Val<br>95 | Ala |
| Asp | Val | Ser | Ile<br>100 | Xaa | Asp | Ser | Val | Ile<br>105 | Ser | Xaa | Ser | Gly | Asp<br>110 | His | Cys |
| Ile | Xaa | Gly<br>115 | Arg | Thr | Leu | Val | Val<br>120 | His | Glu | Lys | Ala | Asp<br>125 | Leu | Gly |
| Lys | Gly | Gly<br>130 | Asn | Glu | Glu | Ser | Thr<br>135 | Lys | Thr | Gly | Asn | Asp<br>140 | Gly | Ser | Arg |
| Xaa | Xaa | Cys | Gly | Val | Ile | Gly | Ile | Ala | Gln |

( 2 ) INFORMATION FOR SEQ ID NO:44:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

```
Met Leu Ser Arg Ala Val Cys Gly Thr Ser Arg Gln Leu Ala Pro Ala
 1               5                  10                  15
Leu Gly Tyr Leu Gly Ser Arg Gln Lys His Ser Leu Pro Asp Leu Pro
                20                  25                  30
Tyr Asp Tyr Gly Ala Leu Glu Pro His Ile Asn Ala Gln Ile Met Gln
                35                  40                  45
Leu His His Ser Lys His His Ala Ala Tyr Val Asn Asn Leu Asn Val
        50                  55                  60
Thr Glu Glu Lys Tyr Gln Glu Ala Leu Ala Lys Gly Asp Val Thr Ala
65                  70                  75                  80
Gln Thr Ala Leu Gln Pro Ala Leu Lys Phe Asn Gly Gly Gly His Ile
                85                  90                  95
Asn His Ser Ile Phe Trp Thr Asn Leu Ser Pro Asn Gly Gly Gly Glu
                100                 105                 110
Pro Lys Gly Glu Leu Leu Glu Ala Ile Lys Arg Asp Phe Gly Ser Phe
                115                 120                 125
Asp Lys Phe Lys Glu Lys Leu Thr Ala Ala Ser Val Gly Val Gln Gly
        130                 135                 140
Ser Gly Trp Gly Trp Leu Gly Phe Asn Lys Glu Arg Gly His Leu Gln
145                 150                 155                 160
Ile Ala Ala Cys Pro Asn Gln Asp Pro Leu Gln Gly Thr Thr Gly Leu
                165                 170                 175
Ile Pro Leu Leu Gly Ile Asp Val Trp Glu His Ala Tyr Tyr Leu Gln
                180                 185                 190
Tyr Lys Asn Val Arg Pro Asp Tyr Leu Lys Ala Ile Trp Asn Val Ile
                195                 200                 205
Asn Trp Glu Asn Val Thr Glu Arg Tyr Met Ala Cys Lys Lys
210                 215                 220
```

( 2 ) INFORMATION FOR SEQ ID NO:45:

( i ) SEQUENCE CHARACTERISTICS:
        ( A ) LENGTH: 240 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Met Leu Ala Leu Leu Cys Ser Cys Leu Leu Leu Ala Ala Gly Ala Ser
 1               5                  10                  15
Asp Ala Trp Thr Gly Glu Asp Ser Ala Glu Pro Asn Ser Asp Ser Ala
                20                  25                  30
Glu Trp Ile Arg Asp Met Tyr Ala Lys Val Thr Glu Ile Trp Gln Glu
                35                  40                  45
Val Met Gln Arg Arg Asp Asp Asp Gly Thr Leu His Ala Ala Cys Gln
        50                  55                  60
```

-continued

| Val 65 | Gln | Pro | Ser | Ala | Thr 70 | Leu | Asp | Ala | Ala | Gln 75 | Pro | Arg | Val | Thr | Gly 80 |
| --- | --- | --- | --- | --- | --- | --- | --- | --- | --- | --- | --- | --- | --- | --- | --- |
| Val | Val | Leu | Phe | Arg 85 | Gln | Leu | Ala | Pro | Arg 90 | Ala | Lys | Leu | Asp | Ala 95 | Phe |
| Phe | Ala | Leu | Glu 100 | Gly | Phe | Pro | Thr | Glu 105 | Pro | Asn | Ser | Ser | Ser 110 | Arg | Ala |
| Ile | His | Val 115 | His | Gln | Phe | Gly | Asp 120 | Leu | Ser | Gln | Gly | Cys 125 | Glu | Ser | Thr |
| Gly | Pro 130 | His | Tyr | Asn | Lys | Leu 135 | Ala | Val | Pro | His | Pro 140 | Gln | His | Pro | Gly |
| Asp 145 | Phe | Gly | Asn | Phe | Ala 150 | Val | Arg | Asp | Gly | Ser 155 | Leu | Trp | Arg | Tyr | Arg 160 |
| Ala | Gly | Leu | Ala | Ala 165 | Ser | Leu | Ala | Gly | Pro 170 | His | Ser | Ile | Val | Gly 175 | Arg |
| Ala | Val | Val | Val 180 | His | Ala | Gly | Glu | Asp 185 | Asp | Leu | Gly | Arg | Gly 190 | Gly | Asn |
| Gln | Ala | Ser 195 | Val | Glu | Asn | Gly | Asn 200 | Ala | Gly | Arg | Arg | Leu 205 | Ala | Cys | Cys |
| Val | Val 210 | Gly | Val | Cys | Gly | Pro 215 | Gly | Leu | Trp | Glu | Arg 220 | Gln | Ala | Arg | Glu |
| His 225 | Ser | Glu | Arg | Lys | Lys 230 | Arg | Arg | Arg | Glu | Ser 235 | Glu | Cys | Lys | Ala | Ala 240 |

METHODS FOR THE DAIGNOSIS, OF FAMILIAL AMYOTROPHIC LATERAL SCLEROSIS

STATEMENT AS TO FEDERALLY SPONSORED RESEARCH

Funding for the work described herein was provided in part by the federal government through N.I.N.D.S. research grant No. IPOINS31248-01. The federal government has certain rights in the invention.

BACKGROUND OF THE INVENTION

The invention relates to cell death diseases.

Neurodegenerative diseases include familial and sporadic amyotrophic lateral sclerosis (FALS and ALS, respectively), familial and sporadic Parkinson's disease, Huntington's disease, familial and sporadic Alzheimer's disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, gilles de la tourette syndrome, and Hallervorden-Spatz disease. Most of the diseases are typified by onset during the middle adult years and lead to rapid degeneration of specific subsets of neurons within the neural system, ultimately resulting in premature death. There is no known cure nor is there an effective therapy to slow the progression for any of the stated diseases.

Amyotrophic lateral sclerosis (ALS) is the most commonly diagnosed progressive motor neuron disease. The disease is characterized by degeneration of motor neurons in the cortex, brainstem and spinal cord (*Principles of Internal Medicine,* 1991 McGraw-Hill, Inc., New York; Tandan et al. *Ann. Neurol,* 18:271–280, 419–431, 1985). Generally, the onset is between the third and sixth decade, typically in the sixth decade. ALS is uniformly fatal, typically within five years (Kurland et al., *Proc Staff Meet Mayo Clin,* 32:449–462, 1957). The cause of the disease is unknown and ALS may only be diagnosed when the patient begins to experience asymmetric limb weakness and fatigue, localized fasciculation in the upper limbs and/or spasticity in the legs which typifies onset.

In ALS the neurons of the cerebral cortex and anterior horns of the spinal cord, together with their homologues in some of the motor nuclei of the brain stem, are affected. The class of neurons affected is highly specific: motor neurons for ocular motility and sphincteric motor neurons of the spinal cord remain unaffected until very late in the disease. Although death occasionally results shortly after the onset of the symptomatic disease, the disease generally ends with respiratory failure secondary to profound generalized and diaphragmatic weakness.

About 10% of ALS cases are inherited as an autosomal dominant trait with high penetrance after the sixth decade (Mulder et al. *Neurology,* 36:511–517, 1986; Horton et al. *Neurology,* 26:460–464, 1976). In almost all instances, sporadic and autosomal dominant familial ALS (FALS) are clinically similar (Mulder et al. *Neurology,* 36:511–517, 1986; Swerts et al., *Genet. Hum,* 24:247–255, 1976; Huisquinet et al., *Genet.* 18:109–115, 1980). It has been shown that in some but not all FALS pedigrees the disease is linked to a genetic defect on chromosome 21q (Siddique et al., *New Engl. J. Med.,* 324:1381–1384, 1991).

Parkinson's disease (paralysis agitans) is a common neurodegenerative disorder which appears in mid to late life. Familial and sporadic cases occur, although familial cases account for only 1–2 percent of the observed cases. The neurological changes which cause this disease are somewhat variable and not fully understood. Patients frequently have nerve cell loss with reactive gliosis and Lewy bodies in the substantia nigra and locus coeruleus of the brain stem. Similar changes are observed in the nucleus basalis of Meynert. As a class, the nigrostriatal dopaminergic neurons seem to be most affected.

The disorder generally develops asymmetrically with tremors in one hand or leg and progresses into symmetrical loss of voluntary movement. Eventually, the patient becomes incapacitated by rigidity and tremors. In the advanced stages the disease is frequently accompanied by dementia.

Diagnosis of both familial and sporadic cases of Parkinson's disease can only be made after the onset of the disease. Anticholinergic compounds, propranolol, primidone and levodopa are frequently administered to modify neural transmissions and thereby suppress the symptoms of the disease, though there is no known therapy which halts or slows the underlying progression. Deprenyl has shown some therapeutic promise.

Huntington's disease is a progressive disease which is always transmitted as an autosomal dominant trait. Individuals are asymptomatic until the middle adult years, although some patients show symptoms as early as age 15. Once symptoms appear, the disease is characterized by choreoathetotic movements and progressive dementia until death occurs 15–20 years after the onset of the symptoms.

Patients with Huntington's disease have progressive atrophy of the caudate nucleus and the structures of the basal ganglia. Atrophy of the caudate nucleus and the putamen is seen microscopically where there is an excessive loss of neural tissue. However, there are no morphologically distinctive cytopathological alterations which have been observed.

Although some of the characteristic mental depression and motor symptoms associated with Huntington's may be suppressed using tricyclic antidepressants and dopamine receptor antagonists, respectively, no therapy exists for slowing or preventing of the underlying disease process. Huntington's disease appears to map to a single locus on chromosome 4 and a linkage test currently exists for the clinical assessment of disease risk in presymptomatic individuals with afflicted relatives. Because the gene for Huntington's disease has not been identified, there is an inherent error rate in the current linkage test.

Hallervorden-spatz disease is a neurodegenerative disease which affects the neurons in the region of the basal ganglia. The symptoms generally appear childhood and adolescence and the disease appears with an inheritance pattern that appears to be autosomal recessive. Patients show abnormalities in muscle tone and movement such a choreoathetosis and dystonia similar to that seen in parkinsonism. As the disease progresses there is increasing dementia. Death generally occurs approximately ten years after onset.

There is no known presymptomatic diagnosis, cure or treatment for Hallervorden-Spatz disease. However, iron toxicity has recently been implicated in the progression of this disease Greenfield, *Neuropathology,* W. Blackwood & J. A. N. Corsellis, Eds. (Edinborgh; T. and A. Constable, Ltd., 1976) pages 178–180. As a result of this implication, the chelating agent deferoxamine mesylate has been administered to patients. However, this therapeutic approach has shown no definite benefit (Harrison's Principles of Internal Medicine, Wilson et al. Eds., McGraw-Hill, Inc., New York, 1991).

Alzheimer's disease is the most important of the neurodegenerative diseases due to the high frequency of occurrence within the population and the fatal course of the disease. Two forms of the disease exist: presenile dementia, in which the symptoms emerge during middle age, and senile dementia which occurs in the elderly. Both forms of the disease appear to have the same pathology. A clear genetic predisposition has been found for presenile dementia. Familial autosomal dominant cases have been reported and the majority of individuals with trisomy 21 (Down's syndrome) develop presenile dementia after the age of 40. The familial Alzheimer's cases map to chromosomes 14, 19 and 21, with more than one locus on 21.

Olivopontocerebellar atrophy is a disease classification which includes a number of disorders characterized by a combination of cerebellar cortical degeneration, atrophy of the inferior olivary nuclei and degeneration and disappearance of the pontine nuclei in the basis pontis and middle cerebellar peduncles. Autosomal dominant inheritance is characteristic in most families. In one family, termed the Schut family, genetic linkage has been shown to chromosome 6. An excess of glutamate has been implicated as the causative agent in this disease. However, there is currently no definitive presymptomatic diagnostic or therapeutic for the treatment of this disease.

The human superoxide dismutases are actually at least three different enzymes: cytosolic Cu/Zn superoxide dismutase encoded by the SOD1 gene on chromosome 21 (Levanon et al., *EMBO J.* 77–84, 1985 and Hjalmarsson et al., *P.N.A.S.* 84:6340–6344, 1987); mitochondrial superoxide dismutase encoded by the SOD2 gene on chromosome 6 (Wispe et al., *Biochim. Biophys. Acta.* 994:30–36, 1989); and extracellular superoxide dismutase encoded by the SOD3 gene on chromosome 4 (Hjalmarsson, supra). SODI, for example, is a homodimeric metalloenzyme that catalyzes the dismutation of the toxic superoxide anion $O_2-$ to $O_2$ and $H_2O_2$. The major function of the superoxide dismutase is to eliminate $O_2-$ resulting from aerobic respiration. As a class of polypeptides present in most living organisms, these enzymes are differentially associated with different metals including iron, manganese, copper and copper-zinc.

In Guam an inherited disease termed Parkinsonism-dementia complex has been described. Clinical, pathological and familial studies have indicated that this disease is a clinical variant of the local form of ALS. Cases of presenile dementia in the absence of ALS or Parkinsonism have also been observed in this population (Kurland et al. In Norris F. H. Jr. and Kurland L. T. eds. *Motor Neuron Diseases: Research on amyotrodhic lateral sclerosis and related disorders.* N.Y.: Grune & Stratton, 1969; 84:28–50; Hirano et al., *Brain* 84:642–661, 1961; and Hirano et al., *Brain* 84:662–679, 1961).

Hallewell et al. (U.S. Pat. No. 5,066,591) describe methods and compositions for the production of human copper/zinc superoxide dismutase polypeptides in microorganisms.

Hallevell (U.S. Pat. No. 5,084,390) describe recombinant Cu/Zn superoxide dismutase polymers having an extended in vivo half-life composed of SOD monomers covalently coupled to each other.

Bruice (International Patent Application No. PCT/US91/06558) describe synthetic enzymes that mimic catalytic activity of superoxide dismutase.

Bracco et al. (P.S.E.B.M. 196:36–41, 1991) have measured the levels of superoxide dismutase in the cerebral spinal fluid of patients with age-related neurodegenerative disorders including ALS, Alzheimer's disease, and a reference group of normal subjects. Bracco et al. report that the superoxide dismutase activity was found to increase with the age of the subject while no significant correlation was found in the ALS and Alzheimer's disease patients. The activity mean values were found to be significantly lower in patients with ALS and Alzheimer's disease.

Liu et al. (Amer. Physiol. Soc. H589-H593, 1989) describe the administration of polyethylene glycol-conjugated superoxide dismutase and catalase to reduce ischemic brain injury in rats.

Olanow (Ann Neurol. 32:52–59, 1992) have proposed free radicals as the cause of neuronal injury in several neurological disorders, including Parkinson's disease and ischemic brain injury.

SUMMARY OF THE INVENTION

In the first aspect, the invention features methods of diagnosing an increased likelihood of developing cell death disease in a patient. The methods include analyzing the DNA of the patient to determine whether the DNA contains a mutation in an SOD coding sequence, such a mutation being an indication that the patient has an increased likelihood of developing a cell death disease. The methods may be used to diagnose a cell death disease, particularly neurodegenerative disease, more particularly Parkinson's disease, Huntington's disease, Alzheimer's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, gilles de la tourette syndrome, and Hallervorden-Spatz disease, and ALS which is familial, sporadic typical, or atypical in nature. These methods may also be used for the diagnosis of a SOD related disease in a fetus.

The methods may include amplifying a SOD-encoding gene of the patient using an SOD-specific primer, and then analyzing the amplified gene. The DNA may be analyzed by nucleotide sequencing, SSCP analysis, RFMP, heteroduplex analysis or RFLP analysis. The amplifying may be carried out by PCR reaction, by reverse transcriptase PCR or by any other method available to obtain a sufficient amount of DNA.

The primer sequence may be derived from SOD1 nucleic acids, SOD2 nucleic acids, SOD3 nucleic acids or nucleic acids from any other human SOD gene.

In the second aspect, the invention features kits for the diagnosis of a cell death disease in a patient. The kits may include one or more SOD gene-specific PCR primers or antibodies recognizing the SOD polypeptides. The PCR primers may include an SOD1-specific nucleic acid sequences, SOD2-specific nucleic acid sequences, SOD3-specific nucleic acid sequences. These kits may be used to diagnose any of the above referenced diseases.

In the third aspect, the invention features methods of treating a patients with a disease involving a mutant SOD encoding gene or environmentally induced ALS. The methods include administering to the patient an antioxidant, effective to reduce the symptoms the disease in the patient. The antioxidant may be a lazaroid, BHA, BHT, Beta-carotene, or any other antioxidant which reduces the level of toxic compounds in the affected cells.

Also included are methods of treating a patient with a disease involving a mutant SOD encoding gene or a patient with sporadic ALS due to environmental causes which include administering to the patient SOD polypeptide, in an amount effective to reduce the symptoms of said disease in said patient. The SOD polypeptide may be SOD Cu/ZnSOD, mSOD, ecSOD, or derivatives, as described below.

Methods of treating the above patients may also include administering to the patient a chelating agent, e.g. desferoxamine, or transgene including a nucleotide sequence encoding a SOD polypeptide e.g., a nucleotide sequence which encodes the Cu/ZnSOD polypeptide, the mSOD polypeptide, or ecSOD polypeptide.

Also included in the invention is method for treating a patient with a disease involving a mutant SOD encoding gene. This method includes first identifying a mutant SOD polypeptide-encoding gene in the DNA of the patient, and, second, administering to the patient a therapeutic amount of the anti-sense RNA homolog of a gene encoding a SOD polypeptide. The polypeptide may be wild-type SOD or a polypeptide encoded by the mutant SOD-encoding gene.

Also included is a method for treating a patient with a disease involving a mutant SOD encoding gene, wherein the mutant SOD polypeptide-encoding gene in the DNA is identified in the patient, and a therapeutic amount of a transgene encoding the wild-type homolog of the mutant SOD polypeptide is administered.

Further included is a method for treating a patient with a disease involving a mutant SOD-encoding gene, which comprises identifying the mutant SOD polypeptide-encoding gene in the DNA of the patient, and administering to the patient a therapeutic amount of a transgene encoding the anti-sense homolog of said wild-type SOD RNA.

Also a part of the invention is a method of treating a patient with a disease involving a mutant SOD encoding gene by administering to the patient an antibody which is sufficient to partially inactivate said mutant SOD polypeptide.

A method of treating a patient with a disease involving a mutant SOD encoding gene or a patient with sporadic ALS due to environmental causes either of whose disease is caused at least in part by excess SOD activity by administering to the patient an inhibitor of wild-type SOD, such as those provided herein, is a part of the invention.

A method of treating a patient with a disease involving a deleterious mutant SOD encoding gene or a patient with sporadic ALS due to environmental causes by the administering of a mutant SOD polypeptide with increased SOD enzymatic activity compared to wild-type SOD is also included as a part of the invention. Such a patient may also be treated by administering a nucleotide sequence encoding a non-wild-type therapeutic SOD polypeptide mutant different from and capable of inhibiting the deleterious SOD polypeptide. As in all methods, this SOD polypeptide may be a fragment of SOD, an analog of SOD, or a non-peptide mimetic of SOD.

Further included is a method of treating a patient with a disease involving a mutant SOD encoding gene by administering to the patient a compound which participates in a biochemical pathway involving a SOD polypeptide. These compounds may include glutathione peroxidase, catalase, or nitric oxide synthase.

Any of the following diseases may be treated using one or more of the above methods: a cell death disease, particularly a neurodegenerative disease, more particularly Parkinson's disease, Huntington's disease, Alzheimer's disease, Hallervorden-Spatz disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, gilles de la tourette syndrome, and Hallervorden-Spatz disease, and ALS which is familial, sporadic typical, or atypical in nature.

In a fourth aspect, the invention features antibodies reactive with a FALS polypeptide but not significantly reactive with a wild-type SOD polypeptide. These antibodies may be monoclonal or polyclonal and may be obtained by subtractive techniques. The antibodies may be sufficient for the inactivation of a SOD polypeptide.

These antibodies may be used as stated above to diagnose ALS in a patient by contacting a serum sample of said patient with the antibody.

In a fifth aspect, the invention features methods of treating a patient with a neoplasm by administering to the patient a FALS polypeptide. A patient with a neoplasm, may also be treated by the administration of transgene encoding an FALS polypeptide.

In the sixth aspect, the invention features a transgenic non-human animal whose somatic and germ cells contain a transgene for a disease-causing mutant SOD polypeptide having a nucleic acid sequence encoding a disease causing SOD polypeptide in an expressible genetic construction. The animal may be a mouse, a worm, or any other animal useful for research or drug development.

In the seventh aspect, the invention features a bacterial or yeast cell containing purified nucleic acid derived from a FALS gene.

The eighth aspect, the invention features purified DNA encoding a purified FALS polypeptide, purified RNA encoding a purified FALS polypeptide, and purified FALS polypeptide.

A ninth aspect of the invention is the use of any of the methods or compounds of the invention which do not solely depend upon the physical properties of a mutant SOD polypeptide for the treatment of a disease of cell death when the defect is due to a mutation in a component of the SOD pathway other than the SOD polypeptide. For example, treatment of diseases due to defects in the production or function of glutathione peroxidase, catalase and nitric oxide synthase. Methods useful for the treatment of these disorders include administration of wild-type and mutant SOD, anti-sense RNA to SOD encoding sequences, use of antibodies to wild-type SOD, and use of analogs and inhibitors of compounds in the SOD pathway.

More specifically, the invention provides therapies using Cu/Zn superoxide dismutase (Cu/ZnSOD), mitochondrial superoxide dismutase (mSOD), or extracellular superoxide dismutase (ecSOD) (FIG. 2–4 and SEQ ID NOS: 1–3, respectively), as well as other naturally occurring superoxide dismutase polypeptides. Also included are: allelic variations; natural mutants; induced mutants; proteins encoded by DNA that hybridizes under high (e.g., washing at 2×SSC at 40° C. with a probe length of at least 40 nucleotides) stringency conditions to naturally occurring Cu/Zn SOD, mSOD, or ecSOD-encoding nucleotide sequences (i.e. SOD1, SOD2, or SOD3; for other definitions of high and low stringency see Current Protocols in Molecular Biology, John Wiley & Sons, New York, 1989, 6.3.1–6.3.6, hereby incorporated by reference). The term "SOD polypeptide" also includes chimeric polypeptides that include Cu/ZnSOD, mSOD, or ecSOD together with unrelated sequences.

The invention also includes any biologically active fragment or analog of Cu/ZnSOD, mSOD or ecSOD. By "biologically active" is meant possessing therapeutically useful superoxide reducing activity which is characteristic of the Cu/ZnSOD, mSOD, or ecSOD polypeptides shown in FIGS. 2–4 (SEQ ID NOS: 1–3). Therapeutically useful activity of a Cu/ZnSOD, MSOD or ecSOD fragment or Cu/ZnSOD, mSOD, or ecSOD analog, can be determined in any of a variety of Cu/ZnSOD, mSOD or ecSOD assays. For example, those assays described in Wayne and Fridovich (Analytical Biochemistry, 161: 559–566 (1987)), McCord and Fridovich (J. of Biol. Chem., 244: 6049–6055 (1969)), and Salin and McCord (J. of Clin. Invest., 54:1005–1009 (1974)) may be used to determine superoxide dismutase activities of Cu/ZnSOD, mSOD or ecSOD. A Cu/ZnSOD, mSOD or ecSOD analog possessing, most preferably 90%, preferably 40%, or at least 10% of the activity of a wild-type or mutant Cu/Zn SOD, mSOD, or ecSOD polypeptide (shown in FIGS. 2–4; SEQ ID NOS: 1–3), in any in vivo or in vitro Cu/ZnSOD, mSOD or ecSOD assay (e.g., those described herein) is considered biologically active and useful in the methods of the invention.

Preferred analogs include 155-amino acid Cu/Zn SOD, 222 amino acid mSOD, or 240 amino acid ecSOD (or biologically active fragments thereof) whose sequences differ from the wild-type sequence only by conservative amino acid substitutions, for example, substitution of one amino acid for another of the same class (e.g., valine for glycine, arginine for lysine, etc.) or by one or more non-conservative amino acid substitutions, deletions, or insertions which do not destroy the polypeptide's relevant biological activity as measured using in vivo or in vitro (e.g., those described above). Preferred analogs also include Cu/ZnSOD, mSOD, or ecSOD (or biologically active fragments thereof) which are modified for the purpose of increasing peptide stability; such analogs may contain, for example, one or more desaturated peptide bonds or D-amino acids in the peptide sequence.

Analogs can differ from naturally occurring Cu/ZnSOD, mSOD, or ecSOD polypeptides by amino acid sequence differences or by modifications that do not involve sequence, or by both. Analogs useful for the methods of the invention will generally exhibit at least 65%, more preferably 80%, even more preferably 90%, and most preferably 95% or even 99%, homology with all or part of a naturally occurring Cu/ZnSOD, mSOD, or ecSOD sequence. The length of comparison sequences will generally be at least about 15 amino acid residues, preferably more than 40 amino acid residues. Modifications include in vivo, or in vitro chemical derivatization of polypeptides, e.g., acetylation, glycosylation, or carboxylation. Also embraced are versions of the same primary amino acid sequence that have phosphorylated amino acid residues, e.g., phosphotyrosine, phosphoserine, or phosphothreonine. Analogs can differ from naturally occurring Cu/ZnSOD, mSOD, or ecSOD polypeptides by alterations of their primary sequence. These include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

The invention also provides methods of using SOD polypeptides (or nucleotide sequences encoding polypeptides) which are obtained from other living organisms which are found to synthesize superoxide dismutases, e.g., *E. coli, Saccharomyces cerevisiae*, and *C. elegans*. Useful mutants of such SOD polypeptides are those which have increased stability or other desirable properties.

The invention also includes therapeutic uses of polypeptides (or nucleotide sequences encoding polypeptides) which are substantially (at least 70%) homologous to wild-type SOD polypeptides or genes. "Homologous" refers to the sequence similarity between two polypeptides or nucleic acids. When a position in both of the two compared sequences is occupied by the same base or amino acid monomeric subunit, e.g., if a position in each of the two DNA molecules is occupied by adenine, then the molecules are homologous at that position. The homology between two sequences is a function of the number of matching or homologous positions shared by the two sequences. For example, if 6 of 10 of the positions in two sequences are homologous, then the two sequences are 60% homologous. By way of example, the DNA sequences ATTGCC and TATGGC are 50% homologous.

Substantially pure Cu/ZnSOD, mSOD, and ecSOD polypeptides can be produced in quantity using standard recombinant DNA-based techniques. Thus, recombinant Cu/ZnSOD, mSOD2, or ecSOD polypeptides can be administered with a pharmaceutically acceptable diluent, carrier, or excipient, in unit dosage form.

Conventional pharmaceutical practice may be employed to provide suitable formulations or compositions to administer the polypeptide to patients suffering from or presymptomatic for a disease of cell death.

Further included as an aspect gene of the invention are the FALS-SOD polypeptides, e.g., those polypeptides encoded by the nucleic acid of patients with FALS due to a SOD mutation. Also included are the nucleic acids which encode these mutant polypeptides. Also included as an aspect of the invention are antibodies, particularly monoclonal antibodies, which are reactive with FALS-SOD polypeptides.

The invention also includes methods of treating or preventing ALS and FALS by the administration of inhibitors and agonists of SOD. This method is appropriate in patients in whom SOD gene which encodes a polypeptide which confers increased SOD enzymatic activity.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of Cu/ZnSOD, mSOD, or ecSOD can be generated by methods known to those skilled in the art. The ability of a candidate fragment to exhibit a biological activity of Cu/ZnSOD, mSOD, or ecSOD can be assessed by methods described below. Also included are Cu/ZnSOD, mSOD, or ecSOD polypeptides containing amino acids that are normally removed during protein processing (for example, the leader sequence of ecSOD), including additional amino acids that are not required for the biological activity of the polypeptide, or including additional amino acids (if any) that result from alternative mRNA splicing or alternative protein processing events.

The invention also provides methods of using SOD polypeptides (or nucleotide sequences encoding polypeptides) which are obtained from other living organisms which are found to synthesize superoxide dismutases, e.g., *E.coli, Saccharomyces cerevisiae*, and *C. elegans*. Useful mutants of such SOD polypeptides are those which have increased stability or other desirable properties.

The invention also includes therapeutic uses of polypeptides (or nucleotide sequences encoding polypeptides) which are substantially (at least 70%) homologous to wild-type SOD polypeptides or genes. "Homologous" refers to the sequence similarity between two polypeptides or nucleic acids. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions share by the two sequences. For example, if 6 of 10 of the positions in two sequences are homologous, then the two sequences are 60% homologous. By way of example, the DNA sequences ATTGCC and TATGGC are 50% homologous.

Substantially pure Cu/ZnSOD, mSOD, and ecSOD polypeptides can be produced in quantity using standard recombinant DNA-based techniques. Thus, recombinant Cu/ZnSOD, mSOD2, or ecSOD polypeptides can be administered with a pharmaceutically acceptable diluent, carrier, or excipient, in unit dosage form.

Conventional pharmaceutical practice may be employed to provide suitable formulations or compositions to administer the polypeptide to patients suffering from or presymptomatic for a disease of cell death. A "substantially pure" preparation of a polypeptide is a preparation which is substantially free (e.g., to the extent required for formulating Cu/ZnSOD, mSOD2, or ecSOD into a therapeutic composition) of the proteins with which it naturally occurs in a cell.

The formulations of the invention can be administered for example, by parenteral, intravenous, subcutaneus, intramuscular, intracranial, intraorbital, opthalmic, intraventricular, intracapsular, intraspinal, intracisternal, intraperitoneal, intranasal, aerosol, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of present factors. Other potentially useful parenteral delivery systems for the factors include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

Toxic SOD mutants and nucleotide sequences encoding such polypeptides can be formulated by any of the above methods for use as therapies for diseases of cell proliferation, e.g., cancer.

Other features and advantages of the invention will be apparent from the following detailed description, and from the claims.

DETAILED DESCRIPTION

The drawings will first be briefly described.
Drawings

FIGS. 1A and 1B and 1C are a set of diagrams illustrating the single-strand conformational polymorphism and sequence analysis of SOD1 exons from FALS-affected individuals. A. is an autoradiogram of single strand conformational polymorphism banding patterns for SOD-1 exons 2(top) and 4(bottom). "N" designates DNA from normal individuals. B is a sequence analysis of SOD1 exons 2 and 4 in genomic FALS DNA. C is a comparison of amino acid sequences from exons 2 and 4 of normal Cu/Zn SOD1 obtained from diverse species, as noted.

FIG. 2 is the genomic sequence of SOD1 and Cu/ZnSOD polypeptide (SEQ ID No. 1).

FIG. 3 is the cDNA sequence of SOD2 and mSOD polypeptide (SEQ ID No. 2).

FIG. 4 is the cDNA sequence of SOD3 and the ecSOD polypeptide (SEQ ID No. 3).

FIG. 5 is a list of primers useful for the diagnosis of diseases linked to the SOD1 nucleic acid sequences.

FIG. 6 is a list of primers for reverse transcriptase PCR for the detection and diagnosis of SOD2 and SOD3 linked diseases.

Figure 1A:
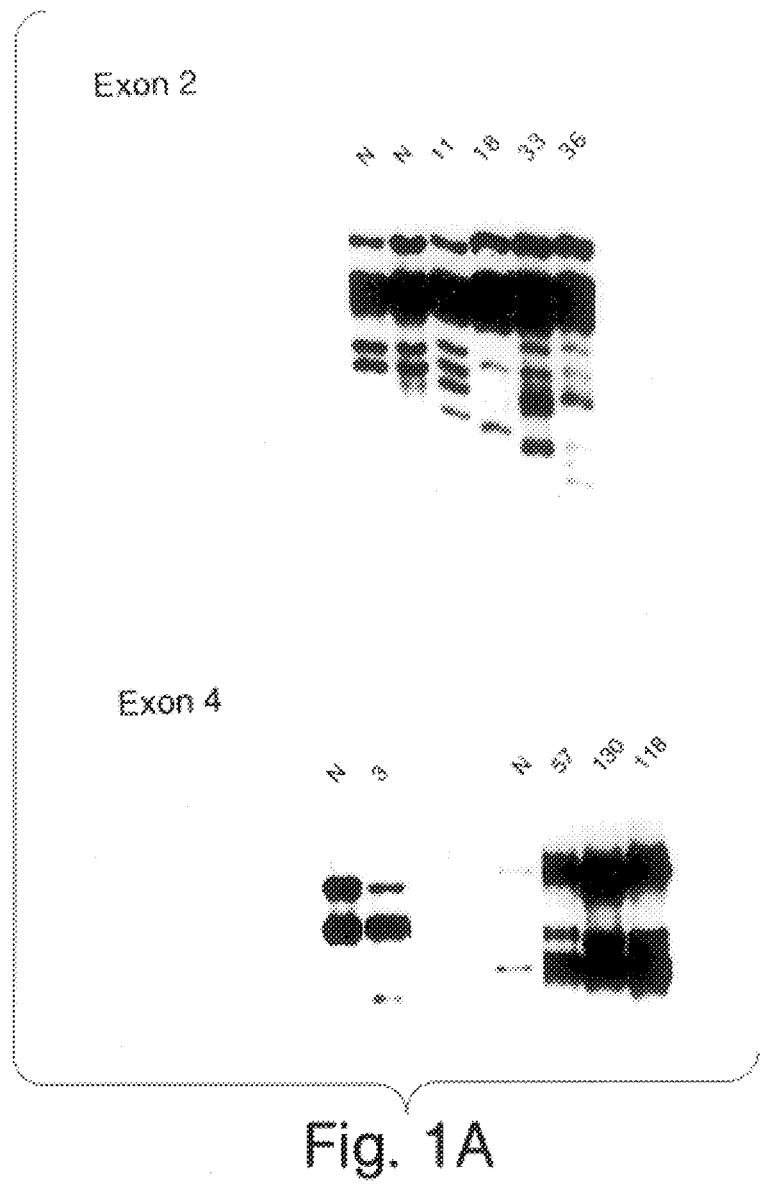

I. Identification of a Class of Genetic Defects Causing Cell Death

Our work has shown that the SOD1 gene is specifically altered in individuals with familial ALS; based on this work, we believe that levels of antioxidant, and particular SOD activity, play a fundamental role in the etiology of diseases of cell death, particularly neurodegenerative diseases such as ALS.

It is a striking fact that a majority of neurodegenerative diseases, ranging from Alzheimer's disease to Parkinson's disease, have a similar profile for onset and progression. These observations support the thesis that a similar mechanism forms the underlying basis of all of these diseases. Our discovery that abnormal SOD is a causative agent in diseases of cell death may provide a missing disease mechanism.

II. Pathogenesis of abnormal SOD1

FIG. 1C is a comparison of amino acid sequences encoded by exons 2 and 4 of Cu/ZnSOD of several disparate organisms: (human [Levanon et al., *EMBO. J.* 77–84, 1985; Hjalmarsson et al., *Proc. Natl. Acad. Sci.,* 84:6340–6344, 1987]; mouse [Bewley, *Nucl. Acids Res.* 16:2728, 1988]; Onchocerca volvulus [Henkle et al., *Infect. Immun.* 59:2063–2069, 1991]; tomato [Perl-Treves et al., *Plant Molec. Biol.* 11:609–623, 1988]; Saccharomyces cerevisiae [Bermingham-McDonogh et al.; *Proc. Natl. Acad. Sci. USA* 85:4789–4793, 1988], all others [Hjalmarsson et al., *Proc. Natl. Acad. Sci.* 84:6340–6344, 1987]). The aberrant FALS residues we discovered are denoted at the top of FIG. 1C; their corresponding positions in the coding sequence are indicated at the bottom of the Figure.

One possibility is that the mutations we discovered decrease or eliminate SOD1 activity. However, most loss-of-function mutations cause a recessive rather than a dominant effect (Muller In *Proceedings of the Sixth International Congress of Genetics,* pp 213–255, 1932; Park et al., *Genetics* 113:821–852, 1986). Exceptions can arise in proliferating cells that allow a somatic mutation to cause a loss of function of the second allele of the gene, as in the case of retinoblastoma (Dryja et al., *Nature* 339:556–558, 1989), but this situation seems unlikely to arise in a non-replicating cell such as the motor neuron.

Another hypothesis is that the putative FALS mutations either increase SOD1 activity or have a dominant-negative effect (Herskowitz, *Nature* 219–222, 1987) such that the mutant SOD1 protein not only is functionally defective but also inhibits the function the normal SOD1 protein expressed from the normal allele. Consistent with the increased activity hypothesis, both Ile-113 and Leu-106 residues are thought to be involved in forming hydrogen bonds important for the increased thermostability of a mutant form of SOD1 (Parge et al., *Proc. Natl. Acad. Sci. USA* 89:6109–6113, 1992); it is plausible that SOD1 proteins with amino acid changes at these residues are of increased stability and hence of increased activity. Consistent with the dominant-negative hypothesis, one of the sites abnormal in FALS patients, Ile-113, has been implicated in hydrogen bond formation between SOD1 monomers (Kitagawa et al., *J. Biochem* 109:477–485, 1991); the normal and mutant proteins may combine to form an inactive heterodimer.

III. Diagnostics for Neurodegenerative disorders

Neurodegenerative disorders may be diagnosed in a patient using the primers provided in FIG. 5 for the SOD1 gene and in FIG. 6 for the SOD2 and SOD3 genes. These primers, or other primers derived from the SOD genes, may be used to identify SOD mutations. For example, diagnosis of individuals with neurodegenerative diseases resulting from mutations in the SOD1 gene may be performed using the techniques provided in the examples, below. Mutations in SOD2 and SOD3 may be diagnosed using the primers which are provided (or any primers which are derived from the SOD2 or SOD3 genes) in combination with the technique of reverse transcriptase PCR (Kawasaki and Wang, *PCR Technology* Evlich, Ed. (New York, Stockton Press, 1989) pages 89–98. Following amplification of the target DNA, SSCP and/or sequence analysis may be performed. It is desirable to compare the sequenced mutation to the equivalent sequences from affected and unaffected relatives in the case of familial diseases. In cases which do not appear to be familial, the mutation is compared to mutations previously observed in the affected population. Correlation with affected relatives, the diseased population, and residues which are conserved through evolution provide an additional measure of certainty useful for a definitive diagnosis.

Neurodegenerative diseases may also be diagnosed using restriction fragment length polymorphisms or any other diagnostic technique involving the detection of nucleotide changes in the SOD genes, e.g., RFMP, and heteroduplex analysis. Knowing the sequences of the SOD genes, one skilled in the art may design combinations of DNA probes and restriction enzymes to determine the afflicted individuals in a FALS (or other inherited SOD disease) family. See also the example, below.

IV. Therapies for Diseases involving a mutant SOD encoding gene

On the basis of our findings, we conclude that toxicity caused by oxygen free radicals is a primary pathogenetspo- mechanism for motor neuron death in FALS and sporadic ALS. Therapeutic measures that diminish this toxicity will blunt the devastating course of these diseases. These therapeutic approaches are also appropriate for the treatment of presymptomatic individuals with defined SOD mutations.

A dominant inheritance pattern is seen in all FALS pedigrees. A dominant phenotype may be conferred by either a dominant negative mutation which decreases the functional level of the SOD complexes or a mutation which increases the SOD enzymatic activity. These dominant FALS mutations may cause loss of function or altered function.

i) Administration of SOD polypeptides

Wild-type SOD polypeptides may be administered to patients with a dominant negative SOD mutation which lowers effective SOD levels in the affected tissue.

Mutant ALS SOD polypeptides identified in FALS patients or created in the laboratory and different from those present in the affected individual may be administered to patients with either dominant negative or gain of function type SOD mutations. Useful polypeptides for this method of complementation are those which, when added to the SOD polypeptide isolated from the affected patient, negates the alteration in SOD enzymatic levels conferred by the mutant SOD polypeptide.

Administration of mutants with increased SOD activity may be used as a method of treating individuals with lowered SOD activity. Such mutants may be naturally occurring, e.g., FALS polypeptides, or constructed in the laboratory. For example, those mutants described by Parge et al. (*P.N.A.S.* 89:6109–6113 (1992)) or Getzoff et al. (*Nature* 358:347–351 (1992)) may be used. FALS polypeptides or nucleic acids altered in the laboratory for therapeutic use may also be administered.

Proteins in which the SOD polypeptide is fused to a ligand may be used for the purpose of stabilizing and/or targeting the useful SOD polypeptides. A fusion protein consisting of a SOD polypeptide, fused to, for example, tetanus toxin, calcium channel blocking agents, transferrin, poliovirus epitopes, neuropeptide fragments, or steroid hormone androgens, or a fragments thereof which are sufficient to target the SOD polypeptide to the motor neurons of an ALS patient may be used.

Proteins which are part of the SOD biochemical pathway may be administered as therapeutics for diseases of cell death, particularly ALS and FALS.

ii) Administration of antioxidants

Figure 7:
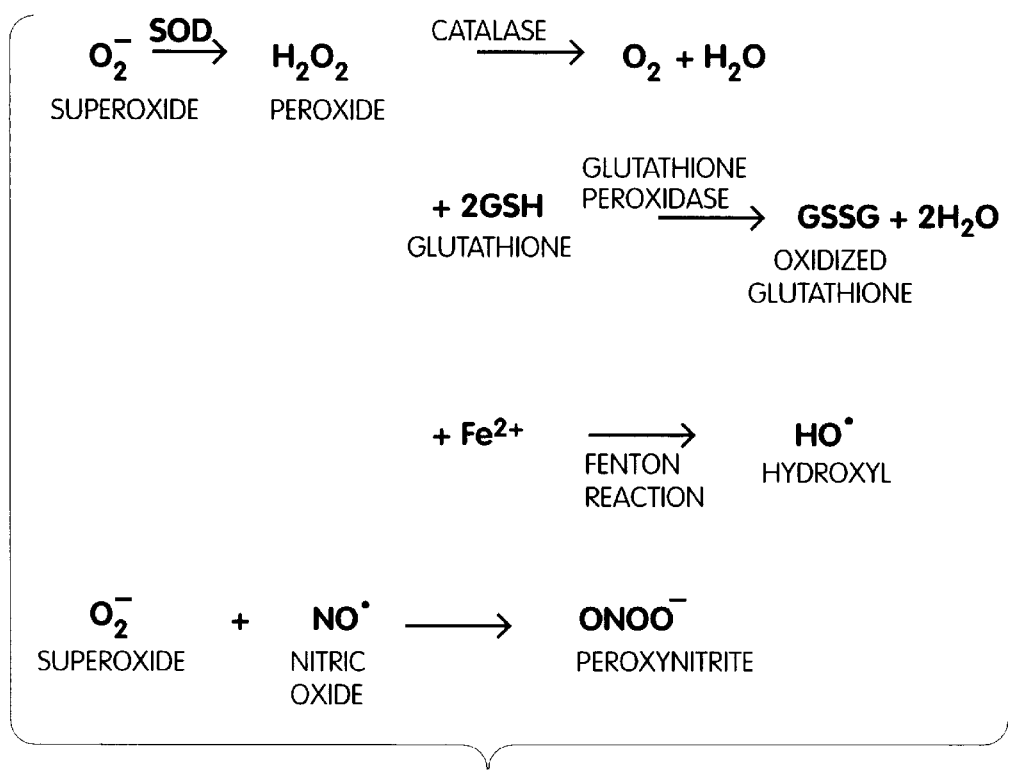
FIG. 7 is a diagram of the pathways for the SOD superoxide dismutase enzymes.

In the SOD biochemical pathway, a decrease in SOD activity results in an increase in the concentration of $O_2$. and an increase in SOD activity results in an increase in HO. (see FIG. 7). Because either an increase or a decrease in SOD activity leads to an increase in free radicals, any antioxidant compound has potential therapeutic value for the treatment of ALS. For example, Vitamin E, Vitamin C, lazaroids (Upjohn, Kalamazoo), BHA, BHT, and beta-carotene are all useful therapeutics.

iii) Administration of chelating agents

Chelating agents, e.g., desferoxamine, known to chelate transition metals involved in the SOD biochemical pathway may be administered for the treatment of a disease involving a mutant SOD gene, e.g., ALS or FALS.

iv) Administration of monoclonal antibodies to SOD polypeptides

Monoclonal antibodies which are specific for the mutant SOD polypeptide may be administered for the treatment of any diagnosed sporadic or familial case of ALS. Polyclonal and monoclonal antibodies which recognize the mutant SOD polypeptide may be obtained using standard techniques known in the art. These antibodies may be subtractive techniques, e.g., by raising polyclonals against mutant SOD, removing those antibodies reactive with normal SOD, and using the remaining antibodies for the preparation of a reagent. The useful monoclonal antibody is an antibody which partially or fully restores the SOD enzymatic activity to the appropriate level in the patient. The desirable antibody may be identified as that antibody which restores SOD levels to within 40% of wild-type levels. Monoclonal antibodies may be tested in vitro by assaying the enzymatic activity of the SOD isolated from a patient in the presence and absence of the monoclonal antibody. Useful antibodies may be used specifically to eliminate the activity of the mutant SOD. This approach utilizes monoclonal antibodies specifically reactive with the mutant polypeptide. In the alternative, when the disease symptoms are the result of excess SOD activity, antibodies to both wild-type and mutant SOD polypeptides are therapeutically useful.

v) Administration of anti-sense RNA

Patients diagnosed with a disease in which a causative agent is a mutant SOD gene may be treated by the administration of anti-sense RNA which is complementary to the mutated region of the SOD gene are anti-sense RNA to wild-type SOD. These anti-sense RNA therapeutics may be synthesized using standard techniques to develop anti-sense RNA therapeutics. Anti-sense RNA which recognizes the mutant sequences may be administered for all genetic forms of SOD disease resulting from a SOD mutation. Anti-sense RNA which recognizes wild-type SOD may be administered to reduce levels of SOD enzymatic activity when the disease is a result of excess SOD.

vi) Administration of inhibitors of SOD

Where the disease is due to an increase in SOD activity inhibitors of SOD may be administered. For example, peptides derived from wild-type or mutant SOD, non-peptide analogs of SOD, or any small molecule inhibitor of SOD, e.g., cyanide, azide or paraquat, may be administered.

vii) Genetic therapy for FALS

Therapeutic Administration of SOD1, SOD2, or SOD3 coding sequences in a Viral Vector Retroviral vectors, or other viral vectors with the appropriate tropism for cells affected by the defective SOD gene, e.g. motor neurons involved in ALS, may be used as a gene transfer delivery system for the SOD1, SOD2, or SOD3 genes which encode therapeutic SOD polypeptides. The useful polypeptides to be encoded are described above. Numerous vectors useful for this purpose are generally known (Miller, *Human Gene Therapy* 15–14, 1990; Friedman, *Science* 244:1275–1281, 1989; Eglitis and Anderson, *BioTechniques* 6:608–614, 1988; Tolstoshev and Anderson, *Current Opinion in Biotechnology* 1:55–61, 1990; Sharp, *The Lancet* 337:1277–1278, 1991; Cornetta et al., *Nucleic Acid Research* and *Molecular Biology* 36:311–322, 1987; Anderson, *Science* 226:401–409, 1984; Moen, Blood Cells 17:407–416, 1991; and Miller and Rosman, *Biotechniques* 7:980–990, 1989; Le Gal La Salle et al., *Science* 259:988–990, 1993). Retroviral vectors are particularly well developed and have been used in a clinical setting (Rosenberg et al., *N. Engl. J. Med* 323:370, 1990). In the case of ALS and FALS, poliovirus and herpes virus vectors, which infect neurons, are particularly useful.

The therapeutic SOD polypeptide may also be administered via a retroviral vector which incorporates into the hematopoetic cells, effectively administering the SOD polypeptide systemically in the presence or absence of targeting sequences.

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors.

Fragments or derivatives of the Cu/ZnSOD, mSOD, or ecSOD polypeptides may also be administered by retroviral gene transfer therapy or another suitable viral vector system. Useful fragments or derivatives of SOD1, SOD2, or SOD3 may be administered by inserting the nucleic acids encoding these fragments or derivatives in place of the complete SOD gene in a gene therapy vector, as described above. Such constructs may be tested using the methods for testing the effects of CuZnSOD, mSOD, or ecSOD on ALS related enzymatic alterations, as described above.

Non viral methods for the therapeutic delivery of nucleic acid encoding Cu/ZnSOD, mSOD, or ecSOD Nucleic acid encoding Cu/ZnSOD, mSOD, or ecSOD, or a fragments thereof, under the regulation of the wild-type promotor and including the appropriate sequences required for insertion into genomic DNA of the patient, or autonomous replication, may be administered to the patient using the following gene transfer techniques: microinjection (Wolff et al., *Science* 247:1465, 1990); calcium phosphate transfer (Graham and Van der Eb, *Virology* 52:456, 1973; Wigler et al., *Cell* 14:725, 1978; Felgner et al., *Proc. Natl. Acad. Sci. USA* 84:7413, 1987); lipofection (Felgner et al., *Proc. Natl. Acad. Sci. USA* 84:7413, 1987; Ono et al., *Neuroscience Lett* 117:259, 1990; Brigham et al., *Am. J. Med. Sci.* 298:278, 1989; Staubinger and Papahadjopoulos, *Meth. Enz.* 101:512, 1983); asialorosonucoid-polylysine conjugation (Wu and Wu, *J. Biol. Chem.* 263:14621, 1988; Wu et al., *J. Biol. Chem.* 264:16985, 1989); and electroporation (Neumnn et al., *EMBO J.* 7:841, 1980).

V. Administration of compounds to prevent the onset of symptomatic FALS

In a patient diagnosed to be at risk for FALS any of the above therapies may be administered before the onset of symptomatic ALS.

VI. Administration of SOD mutant polypeptides for treatment of neoplasms

Cytotoxic mutant SOD polypeptides can be used to treat neoplasms. Such cytotoxic compounds may be administered using any of the known methods for administering cancer chemotherapeutic agents.

VII. Treatment of sporatic ALS caused by environmental factors.

All therapeutic approaches described herein which alter SOD enzymatic levels or affect reactant or product levels within the SOD biochemical pathway but do not hinge on specific characteristics of the mutant polypeptide, may be used with sporadic ALS which is not the result of a genetic defect.

VIII. Diagnosis and Treatment of diseases resulting from mutations in genes encoding non-SOD polypeptides of the SOD biosynthetic pathway.

Diseases caused by deleterious mutations in other polypeptides normally active in the SOD biosynthetic pathway, e.g., catalase, glutathione peroxidase, and nitric oxide synthase, may be diagnosed and treated using the above methods. The above treatments alter SOD activity and the administration of therapies which alter SOD activity will restore the imbalance caused by the perturbations elsewhere in the pathway.

The following examples are to illustrate not limit the invention.

EXAMPLE

I. Identification of the Causative Gene in Familial ALS

Described here is the identification of fourteen different SOD1 missense mutations in sixteen different FALS families. Additionally, mutations have been detected by SSCP but not sequenced in five families.

A) Methods

Methods: PCR primers are used in the analysis of SOD1 were:

Exon 2:

Set a 5' ACTCTCTCCAACTTTGCACTT 3' (SEQ ID NO: 6)   5'CCCACCTGCTGTATTATCTCC 3' (SEQ ID NO: 7)
Set b 5' TTCAGAAACTCTCTCCAACTT 3' (SEQ ID NO: 8)   5'CGTTTAGGGGCTACTCTACTGT 3' (SEQ ID NO: 9)

Exon 4:

Set a 5' CATATAAGGCATGTTGGAGACT 3' (SEQ ID NO: 10)   5' TCTTAGAATTCGCGACTAACAATC 3' (SEQ ID NO: 11)
Set b 5' CATCAGCCCTAATCCATCTGA 3' (SEQ ID NO: 12)    5' CGCGACTAACAATCAAAGTGA 3' (SEQ ID NO: 13)

PCR amplification was performed on Perkin Elmer Cetus or MJ Research thermal cyclers. The program for amplification was as follows: 2 minutes, 95° C. initial denaturation; 1 minute each at 95° C., 60° C. and 72° C., entrained for 32 cycles; 6 minutes at 72° C. final extension. The expected product sizes for exons 2 and 4 are respectively 132 and 214 bp for primer sets a, and 207 and 236 for primer sets b. SSCP analysis was performed using MDER gels using the manufacturer's recommended protocol (J. T. Baker). Gels containing 5% glycerol were run at room temperature at 4 W for 16 hours. Gels were dried and exposed to film for autoradiography. Sequencing of PCR-amplified exon DNA was performed by purifying the resulting product with Centracon columns (Amicon) and directly sequencing the DNA using Sequenase kits (U.S. Biochemicals).

B) Demonstration of linkage

A CA-dinucleotide repeat D21S223 has been identified in cosmid 21–4.25 from the FALS-linked region.

Using the CA-dinucleotide repeat in Cosmid 21–4.25 from the FALS-linked region we have now found that exon 2 of SOD1 can be amplified by the polymerase chain reaction (PCR) from this cosmid. This indicates very close proximity of D21S223 and the SOD1 gene. We have confirmed the linkage of D21S223, and therefore SOD1, to FALS: D21S223 produces the highest lod scores yet detected (Table 1). Using the program HOMOG (Ott et al. *J. Am. J. Hum. Genetics* 28:528–529, 1976; Ott *Analysis of Human Genetics* 203–216, 1991), we have identified a subset of six of these FALS families in which the disease displays no recombination with D21S223 (Table 1, z=6.8 at theta=0) and is likely to be tightly linked to SOD1; nine additional families have also been shown to display significant linkage to the SOD1 region of chromosome 21.

C) Design of PCR primers and SBCP Analysis

To determine if FALS is associated with mutations in the SOD1 gene, PCR primers were designed for two of the five SOD1 exons based on the published sequence for human SOD1 (Levanon et al., *EMBO J.* 77–84, 1985; Hallewell et al., *Superoxide Dismutase in Chemistry. Biology and Medicine* 249–256, 1986). These primers were used for PCR amplification of SOD1 exonic DNA from genomic DNA of normal, control individuals and of single FALS-affected individuals from families tightly linked either to SOD1 or neighboring markers on chromosome 21q. The products of the PCR reactions were denatured and separated on a polyacrylamide gel (0.5×MDE, J. T. Baker) for single-strand conformational polymorphism (SSCP) analysis, which detects mobility shifts of single-strand DNA caused by sequence variations (Orita et al., *Genomics* 5:874–879, 1989). Autoradiograms of these gels revealed shifts in band mobility for 6 of the 15 families linked to the SOD1 region of chromosome 21q. An additional 12 FALS families also revealed anomalous SSCPs; these families were too small for significant linkage analysis. Five of the FALS families are excluded from linkage to chromosome 21q (table 2); none showed abnormal SSCPs. Figure 1a shows the data for SSCP analysis of SOD1 exons amplified by PCR from lymphocytes of normal and FALS-affected individuals. Specifically FIG. 1A is an autoradiogram showing variations in single-strand conformational banding patterns between normal and FALS DNA for SOD1 exons 2 (top) and 4 (bottom). "N" designates lanes with DNA from normal individuals. The numbers designate lanes with FALS DNA samples and correspond to family numbers in panel B and in Table 3. No band shifts were detected in control DNA samples from normal individuals (140 and 112) respectively for exons 2 and 4 (Table 2).

SSCP analysis was then performed on all available DNA samples from members of families 3, 11, and 192C. In each family, all affected individuals displayed the same band pattern as the originally characterized FALS patient. Additionally, in other family members determined by haplotype analysis to be at risk for FALS, the FALS haplotype cosegregated with the distinctive SSCP variant.

D) Sequencing of SOD1 in affected families

Direct sequencing of PCR-amplified DNA from exons 2 and 4 was performed for 16 of the 23 FALS families with anomalous SSCP bands. In each instance, there was heterozygosity in the DNA sequence indicative of one normal and one abnormal chromosome. As summarized in Table 3, we identified single base pair changes in all 13 of these families. These 13 mutations predict eleven distinct amino acid substitutions. Two different amino acid substitutions were detected in each of two codons (41 and 93; Table 3). In each of two codons (37 and 113), two apparently unrelated families have the same mutation. The same mutation in codon 93 was detected independently in two branches of the same family (designated 3 and 3–192C, Table 3).

Figure 1B:
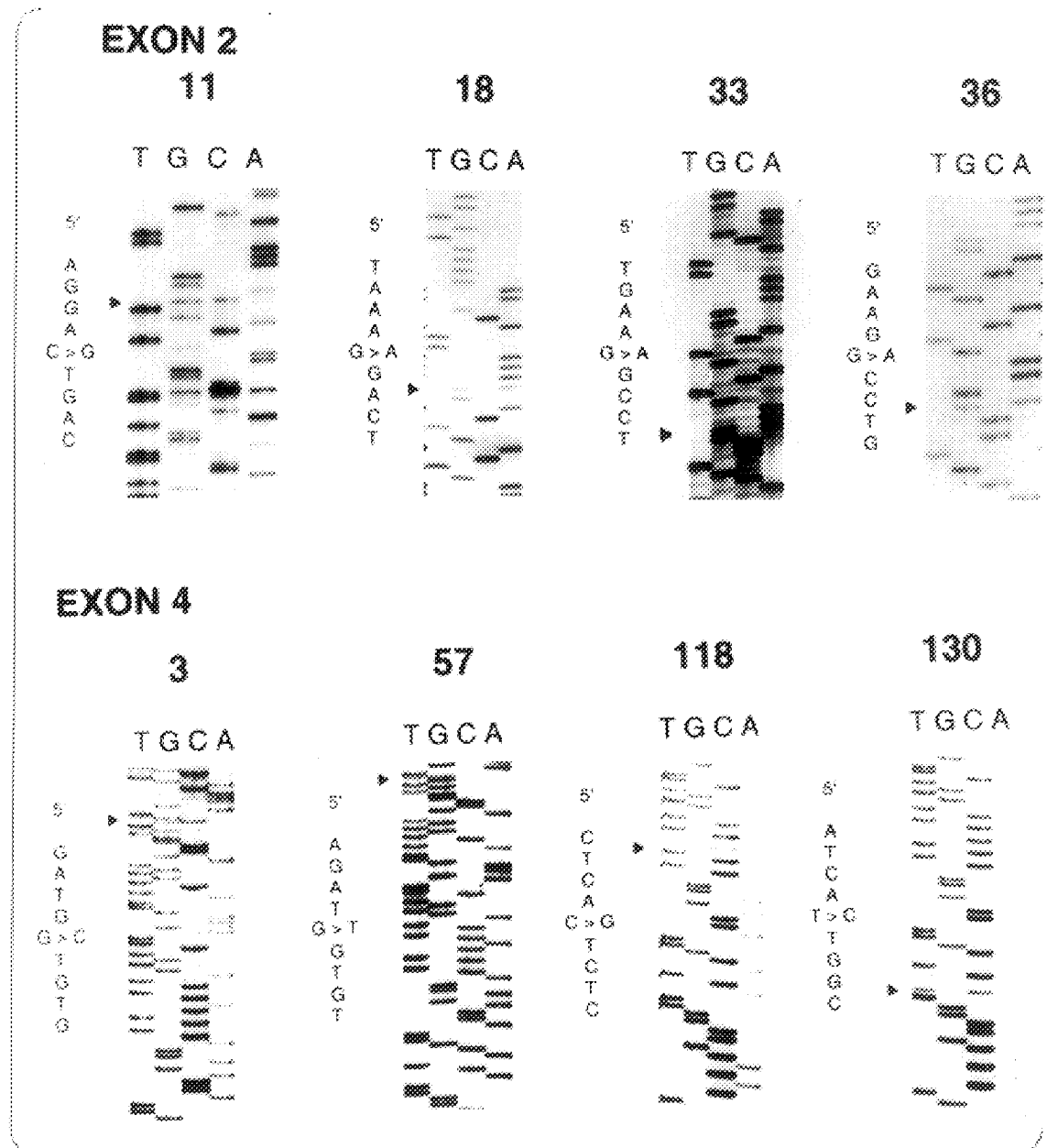

Representative data is shown in FIG. 1B. FIG. 1B are sequence analysis of SOD1 exons amplified by PCR from genomic DNA from lymphocytes of normal and FALS-affected individuals specifically shown in sequence analysis of SOD1 exons 2 and 4 in genomic FALS DNA; the numbers above each sequence ladder identify the affected family, corresponding to family numbers in panel A and in Table 3. The vertically oriented sequence to the left of each ladder designates nine base pairs of sequence including the mutation, indicated by a double base pair, with the wild-type base on the left; the arrowhead denotes the position within the sequence showing heterozygosity as indicated by two (normal and FALS) base pairs. Sequence ladders read 5'→3' from top to bottom.

Nine of the eleven sequence changes alter recognition sites for restriction enzymes (Table 3). For example, in family 11, a new MaeIII site (GTNAC) results from the C→G transition (normal sequence CTGAC). To confirm these sequence changes, we digested PCR products of the corresponding exons with the appropriate restriction enzymes. MaeIII digestion of the exon 2 PCR product for affected members of family 11 produced three bands on a denaturing acrylamide gel (Sequagel 6 (National Diagnostics)): a 132 bp full length product and products of 72 and 60 bp, the fragment sizes expected given the extra MaeIII site in the mutant DNA. These fragments were not detected in normal, control DNA samples from 70 unrelated members of our ALS families or from 73 unrelated members of reference pedigrees in the Center d'Etude du Polymorphiseme Humain (CEPH, (Dausset et al., *Genomics* 6:575–577, 1990)). The base pair changes in families 3, 118, 130 and 684C introduce other novel restriction sites; additionally, in families 33, 36, 130, and 684C. the single-base changes eliminate restriction sites normally present in SOD1.

These changes occur in all 13 of these families. These 13 mutations predict eleven distinct amino acid substitutions. Two different amino acid substitutions were detected in each of two codons (41 and 93; Table 3). In each of two codons (37 and 113), two apparently unrelated families have the same mutation. The same mutation in codon 93 was detected independently in two branches of the same family (designated 3 and 3–193C, Table 3).

These studies identify eleven single amino acid changes in SOD1 based upon the genomic DNA sequences of members of thirteen different FALS families. These changes were not detected in more than 100 chromosomes from normal individuals and thus it may be concluded that these mutations are not simply normal allelic variants. Instead, these mutations occur in tight association with FALS. It is concluded that the mutations identified herein in the SOD1 gene are the mutations which cause FALS.

TABLE 1

Linkage Analysis of FALS Pedigrees with SOD1 Marker D21S223 (DB1)

| | Lod Score | | | | | | |
|---|---|---|---|---|---|---|---|
| Theta | 0 | 5 | 10 | 15 | 20 | 25 | 30 |
| All families[1] | -∞ | 3.83 | 4.25 | 4.05 | 3.55 | 2.87 | 2.11 |
| 21-linked families[2] | 6.80 | 6.05 | 5.26 | 4.44 | 3.61 | 2.77 | 1.93 |

[1]-Data are tabulated from an analysis of 12 families in the Boston arm of the FALS collaborative study (7,11).
[2]-A subset of six families with a high (>80%) posterior probability of linkage to D21S223 as defined using the program HOMOG (12). Some of the eleven mutations described in Table 3 were detected in DNA from members of FALS families too small for significant linkage analysis. Such families could not be included in the linkage data summarized in this Table.

TABLE 2

17 Single-Strand Conformational Polymorphisms in Exons 2 and 4 of SOD1 in FALS DNA[1]

| | All FALS[2] | FALS-21[3] | Control[4] |
|---|---|---|---|
| EXON 2 | | | |
| Normal | 148 | 15[5] | 140 |
| Variant | 7[6] | 1 | 0[7] |
| EXON 4 | | | |
| Normal | 150 | 15 | 112 |
| Variant | 11[8] | 5 | 0 |

[1]See legend for Figure 1 for Methods.
[2]Familial ALS
[3]Subset of families linked by HOMOG (12) to SOD1 (Boston) or adjacent markers (Chicago).
[4]DNA samples from normal individuals unrelated to members of FALS families.
[5]Six from Boston and nine from Chicago FALS pedigrees.
[6]Includes four, two and one samples respectively from Boston, Chicago and Montreal FALS pedigrees.
[7]12 control DNA samples revealed weak and somewhat variable SSCPs; all were normal by sequence analysis.
[8]Includes five, five and one samples respectively from Boston, Chicago and Montreal FALS pedigrees.

TABLE 3A

Base Pair Changes in SOD-1

| family | exon | amino acid | codon | new codon | new amino acid |
|---|---|---|---|---|---|
| 103 | 1 | ala 4 | GCC | GTC | val |
| 104 | 1 | ala 4 | GCC | GTC | val |
| 114 | 1 | ala 4 | GCC | GTC | val |
| 127 | 1 | ala 4 | GCC | GTC | val |
| 18 | 2 | gly 37 | GGA | AGA | arg |
| 594C | 2 | gly 37 | GGA | AGA | arg |
| 11 | 2 | leu 38 | CTG | GTG | val |
| 33 | 2 | gly 41 | GGC | AGC | ser |
| 36 | 2 | gly 41 | GGC | GAC | asp |
| 220C | 2 | his 43 | CAT | CGT | arg |
| 9967C | 4 | gly 85 | GGC | CGC | arg |
| 57 | 4 | gly 93 | GGT | TGT | cys |
| 3 | 4 | gly 93 | GGT | GCT | ala |
| 3-192C | 4 | gly 93 | GGT | GCT | ala |
| 37 | 4 | glu 100 | GAA | GGA | gly |
| 684C | 4 | glu 100 | GAA | GGA | gly |
| 118 | 4 | leu 106 | CTC | GTC | val |
| 130 | 4 | ile 113 | ATT | ACT | thr |
| 385C | 4 | ile 113 | ATT | ACT | thr |
| 78 | 5 | leu 144 | TTG | TCG | ser |
| 113 | 5 | ala 145 | GCT | ACT | thr |

TABLE 3B

SOD1 Mutations in Familial Amyotrophic Lateral Sclerosis

| Family | Base Pair Change | Amino Acid Change | Predicted Restriction Enzyme Change | PCR Product (bp)[1] | Restriction Fragments (bp) Normal | FALS-Specific[2] |
|---|---|---|---|---|---|---|
| Exon 2 | | | | | | |
| 18, 594C | GGA → AGA | gly 37 → arg | | | | |
| 11 | CTG → GTG | leu 38 → val | +MaeIII[3,4] | 132 | 132 | 72, 60 |
| 33 | GGC → AGC | gly 41 → ser | -HaeIII[5] | 132 | 83, 49 | 132 |
| | | | -StuI | 132 | 83, 49 | 132 |
| | | | -Eco57I | 132 | 97, 35 | 132 |
| 36 | GGC → GAC | gly 41 → asp | -HaeIII[3,5] | 132 | 83, 49 | 132 |
| 220C | CAT → CGT | his 43 → arg | -NlaIII | 132 | 87, 30, 9, 6 | 96 |

TABLE 3

SOD1 Mutations in Familial Amyotrophic Lateral Sclerosis

| Family | Base Pair Change | Amino Acid Change | Predicted Restriction Enzyme Change | PCR Product (bp) | Normal | FALS-Specific |
|---|---|---|---|---|---|---|
| Exon 4 | | | | | | |
| 9967C | GGC → CGC | gly 85 → arg | +HinPI | 214 | 214 | 192, 22 |
| | | | +HhaI | 214 | 214 | 192, 22 |
| | | | +FspI | 214 | 214 | 193, 21 |
| 57 | GGT → TGT | gly 93 → cys | | 214 | | |
| 3, 3-192C[6] | GGT → GCT | gly 93 → ala | +SfaNI[3] | 214 | 112, 100 | 72, 40 |
| 684C | GTT → GGA | glu 100 → gly | +Eco57I | 214 | 148, 66 | |
| | | | -MboII | 88, 68, 58 | 165 | |

TABLE 3-continued

SOD1 Mutations in Familial Amyotrophic Lateral Sclerosis

Exon 4

| 118 | CTC → GTC | leu 106 → val | +DdeI[3,4] | 214 | 120, 89, 5 | 83, 6 |
| --- | --- | --- | --- | --- | --- | --- |
| 130, 385C | ATT → ACT | ile 113 → thr | +BsrI[3,4] | 214 | 124, 90 | 113, 11 |
| | | | −BslI[3] | 214 | 116, 98 | 214 |
| | | | −EaeI | 214 | 104, 57, 53 | 161 |

TABLE 3-continued

SOD1 Mutations in Familial Amyotrophic Lateral Sclerosis

Exon 4

Based on primer sets a (see Figure Legend).

Other size products are predicted but not listed because they are not FALS-specific.

Predicted changes in indicated restriction fragments have been confirmed in genomic DNA from FALS patients.

The FALS MaeIII, DdeI and BsrI fragments were not seen in DNA respectively from 143, 73 and 73 control individuals.

All 73 DNA samples from normal controls showed the expected HaeIII restriction site.

The suffix C denotes families analyzed in Chicago. Families 3 and 3-192C are different branches of the same pedigree.

We claim:

1. A method of diagnosing an increased likelihood of developing familial ALS in a patient, said method comprising analyzing the DNA of said patient to determine whether said DNA contains a mutation in a SOD1 gene, such a mutation being an indication that said patient has an increased likelihood of developing familial ALS.

2. The method of claim 1, wherein said analysis comprises amplifying SOD1-encoding nucleic acid of said patient using a SOD1 primer, and then analyzing said nucleic acid.

3. The method of claim 1, wherein said analysis is carried out by nucleotide sequencing.

4. The method of claim 1, wherein said analysis is carried out by SSCP analysis.

5. The method of claim 1, wherein said analysis is carried out by RFLP analysis.

6. The method of claim 2, wherein said amplifying is carried out by PCR reaction.

7. The method of claim 2, wherein said amplifying is carried out by reverse transcriptase PCR.

8. A method of diagnosing a fetus with an increased likelihood of developing familial ALS, said method comprising analyzing the DNA of said fetus to determine whether said DNA contains a mutation in a SOD1 coding sequence, such a mutation being an indication that said fetus has an increased likelihood of developing familial ALS.

9. A method of claim 8, wherein said SOD sequence from said fetus is compared to a SOD coding sequence of a relative of said fetus.

10. The method of claim 1, wherein mutation is a mutation of Ala to Val at amino acid 4.

11. The method of claim 1, wherein mutation is a mutation of Gly to Arg at amino acid 37.

12. The method of claim 1, wherein mutation is a mutation of Leu to Val at amino acid 38.

13. The method of claim 1, wherein mutation is a mutation of Gly to Ser at amino acid 41.

14. The method of claim 1, wherein mutation is a mutation of Gly to Asp at amino acid 41.

15. The method of claim 1, wherein mutation is a mutation of His to Arg at amino acid 43.

16. The method of claim 1, wherein mutation is a mutation of Gly to Arg at amino acid 85.

17. The method of claim 1, wherein mutation is a mutation of Gly to Lys at amino acid 93.

18. The method of claim 1, wherein mutation is a mutation of Gly to Ala at amino acid 93.

19. The method of claim 1, wherein mutation is a mutation of Glu to Gly at amino acid 100.

20. The method of claim 1, wherein mutation is a mutation of Leu to Val at amino acid 106.

21. The method of claim 1, wherein mutation is a mutation of Ile to Thr at amino acid 113.

22. The method of claim 1, wherein mutation is a mutation of Leu to Ser at amino acid 144.

23. The method of claim 1, wherein mutation is a mutation of Ala to Thr at amino acid 145.

* * * * *

UNITED STATES PATENT AND TRADEMARK OFFICE
CERTIFICATE OF CORRECTION

PATENT NO. : 5,843,641
DATED : December 1, 1998
INVENTORS : Robert Brown, H. Robert Horvitz, and Daniel R. Rosen It is certified that error appears in the above-identified patent and that said Letters Patent is hereby corrected as shown below:

On the first page, in the title replace "DAIGNOSIS," with --DIAGNOSIS--;

On the first page, in U.S. patent documents replace cited: "11/1991 Hallewell et al." with --11/1981 Hallewell et al.--;

On the first page, in other publications, in Bracco. F. citation replace "Polargraphic" with --Polarographic--;

On the first page, in other publications, in Hallewell R.A. citation replace "Dismutascin" with --Dismutase in--;

On the first page, in other publications, in Hallewell, B. citation replace "Hallewell" with --Halliwell--;

On the first page, in other publications, in Hartman citation replace "Hypotheses38:75" with --Hypotheses, 38:75--;

On the first page, in other publications, in Hudson citation replace "Laternal" with --Lateral--; and replace "Desmentia" with --Dementia--;

On the first page, in other publications, in McCord citation replace "an" with --An--;

On the first page, in other publications, in Oury citation replace "$O_{2\,toxicity}$" with --$O_2$ toxicity--;

At Col. 1, line 1 replace "DAIGNOSIS" with --DIAGNOSIS--;

UNITED STATES PATENT AND TRADEMARK OFFICE
CERTIFICATE OF CORRECTION

PATENT NO.  5,843,641
DATED       December 1, 1998
INVENTORS   Robert Brown, H. Robert Horvitz, and Daniel R. Rosen It is certified that error appears in the above-identified patent and that said Letters Patent is hereby corrected as shown below:

At Col. 2, line 48 replace "Hallervorden-spatz" with --Hallervorden-Spatz--;

At Col. 3, line 34 replace "SODI" with --SOD1--;

At Col. 3, line 49 replace "amyotrodhic" with --amyotrophic--;

At Col. 3, line 57 replace "Hallevell" with --Hallewell--;

At Col. 7, line 3 replace "MSOD" with --mSOD--;

At Col. 11, line 55 replace "pathogenetspo" with --pathogenetic--;

At Col. 13, line 42 replace "and" with --*and*--;

At Col. 13, line 44 replace "Blood Cells" with --*Blood Cells*--;

At Col. 15, line 18 replace "MDER" with --MDE$^R$--;

At Col. 15, line 44 replace "SBCP" with --SSCP--;

UNITED STATES PATENT AND TRADEMARK OFFICE
CERTIFICATE OF CORRECTION

PATENT NO. : 5,843,641
DATED : December 1, 1998
INVENTORS : Robert Brown, H. Robert Horvitz, and Daniel R. Rosen It is certified that error appears in the above-identified patent and that said Letters Patent is hereby corrected as shown below:

In the tables, at Col. 18 replace "TABLE 3" with --TABLE 3C--;

In the tables, at Col. 19 replace "TABLE 3-continued" with --TABLE 3C-continued--;

In the tables, at Col. 20 replace "TABLE 3-continued" with --TABLE 3C-continued--;

Signed and Sealed this

Eighteenth Day of January, 2000

Attest:

Q. TODD DICKINSON

*Attesting Officer*  *Commissioner of Patents and Trademarks*